US007771735B2

(12) United States Patent
Dvoracek et al.

(10) Patent No.: US 7,771,735 B2
(45) Date of Patent: Aug. 10, 2010

(54) ABSORBENT ARTICLES WITH COMPOSITIONS FOR REDUCING IRRITATION RESPONSE

(75) Inventors: Barbara Jo Dvoracek, Appleton, WI (US); David John Tyrrell, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1706 days.

(21) Appl. No.: 10/406,957

(22) Filed: Apr. 3, 2003

(65) Prior Publication Data

US 2003/0206979 A1 Nov. 6, 2003

Related U.S. Application Data

(63) Continuation-in-part of application No. 09/747,382, filed on Dec. 22, 2000, now Pat. No. 6,749,860, and a continuation-in-part of application No. 09/746,888, filed on Dec. 22, 2000.

(51) Int. Cl.
*A01N 25/00* (2006.01)
*A61K 9/70* (2006.01)

(52) U.S. Cl. .................. 424/404; 424/402; 424/443
(58) Field of Classification Search .................. 424/400
See application file for complete search history.

(56) References Cited

U.S. PATENT DOCUMENTS

| 3,305,392 A | 2/1967 | Britt |
| 3,489,148 A | 1/1970 | Duncan et al. |
| 3,585,998 A | 6/1971 | Hayford et al. |
| 3,724,465 A | 4/1973 | Duchane |
| 3,756,238 A | 9/1973 | Hanke |
| 3,814,101 A | 6/1974 | Kozak |
| 3,821,350 A | 6/1974 | Suchane |
| 3,881,488 A | 5/1975 | Delanty et al. |
| 3,896,807 A | 7/1975 | Buchalter |
| 3,902,493 A | 9/1975 | Baier et al. |
| 4,040,857 A | 8/1977 | Lissant |
| 4,100,324 A | 7/1978 | Anderson et al. |
| 4,164,563 A | 8/1979 | Chang |

(Continued)

FOREIGN PATENT DOCUMENTS

CA 2019557 A1 12/1990

(Continued)

OTHER PUBLICATIONS

Patent Abstracts of Japan 02043265 A: Description of Masaru et al., "Thixotropic Semisolid Composition."

(Continued)

*Primary Examiner*—Robert A Wax
*Assistant Examiner*—Melissa S Mercier
(74) *Attorney, Agent, or Firm*—David J. Arteman; Bryan R. Rosiejka

(57) ABSTRACT

The present invention relates to compositions and absorbent articles including compositions for protecting the skin barrier. The compositions can be applied to the bodyfacing surfaces of absorbent articles so that the compositions come into contact with the skin. The compositions of the invention provide several benefits including prevention and alleviation of skin irritations associated with the use of absorbent articles. The compositions can include hydrophilic and non-aqueous components as well as extracted botanical actives.

14 Claims, 3 Drawing Sheets

U.S. PATENT DOCUMENTS

| | | | |
|---|---|---|---|
| 4,226,889 A | 10/1980 | Yuhas | |
| 4,273,786 A | 6/1981 | Kraskin | |
| 4,343,783 A | 8/1982 | Hooper et al. | |
| 4,355,020 A | 10/1982 | Kuy | |
| 4,355,046 A | 10/1982 | Suess | |
| 4,556,560 A | 12/1985 | Buckingham | |
| 4,604,313 A | 8/1986 | McFarland et al. | |
| 4,613,447 A | 9/1986 | Hara et al. | |
| 4,623,339 A | 11/1986 | Ciraldo et al. | |
| 4,634,438 A | 1/1987 | Sustmann et al. | |
| 4,634,439 A | 1/1987 | Sustmann et al. | |
| 4,637,820 A | 1/1987 | Marini et al. | |
| 4,655,756 A | 4/1987 | Fawkes | |
| 4,657,537 A | 4/1987 | Zimmerer | |
| 4,675,014 A | 6/1987 | Sustmann et al. | |
| 4,685,909 A | 8/1987 | Berg et al. | |
| 4,711,780 A | 12/1987 | Fahim | |
| 4,732,797 A | 3/1988 | Johnson et al. | |
| 4,738,678 A | 4/1988 | Paulis | |
| 4,753,643 A | 6/1988 | Kassai | |
| 4,753,647 A | 6/1988 | Curtis | |
| 4,760,096 A | 7/1988 | Sakai et al. | |
| 4,772,501 A | 9/1988 | Johnson et al. | |
| 4,790,836 A | 12/1988 | Brecher | |
| 4,790,840 A | 12/1988 | Cortina | |
| 4,798,603 A | 1/1989 | Meyer et al. | |
| 4,808,175 A | 2/1989 | Hansen | |
| 4,834,737 A | 5/1989 | Khan | |
| 4,861,405 A | 8/1989 | Kassai | |
| 4,882,204 A | 11/1989 | Tenenbaum | |
| 4,904,524 A | 2/1990 | Yoh | |
| 4,911,932 A | 3/1990 | Clum et al. | |
| 4,931,052 A | 6/1990 | Feldman | |
| 4,960,592 A | 10/1990 | Hagen et al. | |
| 4,970,220 A | 11/1990 | Chaussee | |
| 4,978,534 A | 12/1990 | Saitoh | |
| 4,990,144 A | 2/1991 | Blott | |
| 4,996,238 A | 2/1991 | Matravers | |
| 5,043,155 A | 8/1991 | Puchalski et al. | |
| 5,049,440 A | 9/1991 | Bornhoeft et al. | |
| 5,091,193 A | 2/1992 | Enjolras et al. | |
| 5,110,593 A | 5/1992 | Benford | |
| 5,139,790 A | 8/1992 | Snipes | |
| 5,141,803 A | 8/1992 | Pregozen | |
| 5,147,576 A | 9/1992 | Montague et al. | |
| 5,176,668 A | 1/1993 | Bernardin | |
| 5,176,672 A | 1/1993 | Bruemmer et al. | |
| 5,192,277 A | 3/1993 | Chung et al. | |
| 5,192,606 A | 3/1993 | Proxmire et al. | |
| 5,194,261 A | 3/1993 | Pichierri | |
| 5,232,691 A | 8/1993 | Lemole | |
| 5,244,668 A | 9/1993 | Snipes | |
| 5,306,486 A | 4/1994 | McCook et al. | |
| 5,336,212 A | 8/1994 | De Francesco | |
| 5,336,692 A | 8/1994 | Gans et al. | |
| 5,350,624 A | 9/1994 | Georger et al. | |
| 5,362,488 A | 11/1994 | Sibley et al. | |
| 5,364,382 A | 11/1994 | Latimer et al. | |
| 5,376,655 A | 12/1994 | Imaki et al. | |
| 5,384,125 A | 1/1995 | DiPippo et al. | |
| 5,409,903 A | 4/1995 | Polak et al. | |
| 5,436,007 A | 7/1995 | Hartung et al. | |
| 5,466,232 A | 11/1995 | Cadieux et al. | |
| 5,482,765 A | 1/1996 | Bradley et al. | |
| 5,486,166 A | 1/1996 | Bishop et al. | |
| 5,490,846 A | 2/1996 | Ellis et al. | |
| 5,496,298 A | 3/1996 | Kuepper et al. | |
| 5,509,915 A | 4/1996 | Hanson et al. | |
| 5,525,346 A | 6/1996 | Hartung et al. | |
| 5,533,990 A | 7/1996 | Yeo | |
| 5,569,230 A | 10/1996 | Fisher et al. | |
| 5,578,310 A | 11/1996 | M'Timkulu et al. | |
| 5,601,871 A | 2/1997 | Krzysik et al. | |
| 5,605,749 A | 2/1997 | Pike et al. | |
| 5,607,760 A | 3/1997 | Roe | |
| 5,607,980 A | 3/1997 | McAtee et al. | |
| 5,609,587 A | 3/1997 | Roe | |
| 5,614,293 A | 3/1997 | Krzysik et al. | |
| 5,618,529 A | 4/1997 | Pichierri | |
| 5,618,850 A | 4/1997 | Coury et al. | |
| 5,631,012 A | 5/1997 | Shanni | |
| 5,635,191 A | 6/1997 | Roe et al. | |
| 5,643,588 A | 7/1997 | Roe et al. | |
| 5,643,899 A | 7/1997 | Elias et al. | |
| 5,648,083 A | 7/1997 | Blieszner et al. | |
| 5,650,218 A | 7/1997 | Krzysik et al. | |
| 5,652,049 A | 7/1997 | Suzuki | |
| 5,652,194 A | 7/1997 | Dyer et al. | |
| 5,658,559 A | 8/1997 | Smith | |
| 5,665,368 A | 9/1997 | Lentini et al. | |
| 5,665,426 A | 9/1997 | Krzysik et al. | |
| 5,693,037 A | 12/1997 | Lee et al. | |
| 5,695,868 A | 12/1997 | McCormack | |
| 5,738,859 A | 4/1998 | Posner | |
| H1732 H | 6/1998 | Johnson | |
| 5,801,107 A | 9/1998 | Everhart et al. | |
| 5,830,487 A | 11/1998 | Klofta et al. | |
| 5,833,973 A | 11/1998 | Dobkowski et al. | |
| 5,843,056 A | 12/1998 | Good et al. | |
| 5,849,314 A | 12/1998 | Dobkowski et al. | |
| 5,855,897 A | 1/1999 | Pelle | |
| 5,855,999 A | 1/1999 | McCormack | |
| 5,856,245 A | 1/1999 | Caldwell et al. | |
| 5,869,033 A | 2/1999 | Schulz | |
| 5,869,075 A | 2/1999 | Krzysik | |
| 5,869,172 A | 2/1999 | Caldwell | |
| 5,871,763 A | 2/1999 | Luu et al. | |
| 5,876,736 A * | 3/1999 | Cohen et al. | 424/401 |
| 5,879,341 A | 3/1999 | Odorzynski et al. | |
| 5,891,126 A | 4/1999 | Osborn et al. | |
| 5,938,649 A | 8/1999 | Ducker et al. | |
| 5,944,705 A | 8/1999 | Ducker et al. | |
| 5,945,110 A | 8/1999 | Vianen et al. | |
| 5,951,990 A | 9/1999 | Ptchelintsev | |
| 5,989,577 A | 11/1999 | Hoath et al. | |
| 5,990,377 A | 11/1999 | Chen et al. | |
| 6,004,566 A | 12/1999 | Friedman et al. | |
| 6,031,147 A | 2/2000 | Gross | |
| 6,034,225 A | 3/2000 | Weidner et al. | |
| 6,051,749 A | 4/2000 | Schulz | |
| 6,066,327 A * | 5/2000 | Gubernick et al. | 424/401 |
| 6,074,672 A | 6/2000 | Dobkowski et al. | |
| 6,075,179 A | 6/2000 | McCormack et al. | |
| 6,093,869 A | 7/2000 | Roe et al. | |
| 6,100,442 A | 8/2000 | Samuelsson et al. | |
| 6,103,245 A | 8/2000 | Clark et al. | |
| 6,107,537 A | 8/2000 | Elder et al. | |
| 6,117,439 A | 9/2000 | Kake | |
| 6,118,041 A | 9/2000 | Roe et al. | |
| 6,120,488 A * | 9/2000 | VanRijswijck et al. | 604/385.28 |
| 6,136,332 A | 10/2000 | Grollier et al. | |
| 6,149,934 A | 11/2000 | Krzysik et al. | |
| 6,152,906 A | 11/2000 | Faulks et al. | |
| 6,153,209 A | 11/2000 | Vega et al. | |
| 6,156,024 A | 12/2000 | Schulte et al. | |
| 6,166,285 A | 12/2000 | Schulte et al. | |
| 6,183,766 B1 | 2/2001 | Sine et al. | |
| 6,193,987 B1 | 2/2001 | Harbeck | |
| 6,217,890 B1 * | 4/2001 | Paul et al. | 424/402 |
| 6,238,682 B1 | 5/2001 | Klofta et al. | |
| 6,287,581 B1 * | 9/2001 | Krzysik et al. | 424/402 |
| 6,294,186 B1 | 9/2001 | Beerse et al. | |
| 6,309,736 B1 | 10/2001 | McCormack et al. | |
| 6,316,030 B1 | 11/2001 | Kropf et al. | |

| | | | |
|---|---|---|---|
| 6,331,305 B1 | 12/2001 | Sang | |
| 6,344,218 B1 | 2/2002 | Dodd et al. | |
| 6,355,022 B1 | 3/2002 | Osborn, III et al. | |
| 6,433,244 B1 | 8/2002 | Roe et al. | |
| 6,485,733 B1 | 11/2002 | Huard et al. | |
| 6,503,236 B1 | 1/2003 | Uitenbroek et al. | |
| 6,506,394 B1 | 1/2003 | Yahiaoui et al. | |
| 6,515,029 B1 | 2/2003 | Krzysik et al. | |
| 6,680,285 B2 * | 1/2004 | Abbas et al. | 510/141 |
| 6,716,441 B1 | 4/2004 | Osborne et al. | |
| 6,793,930 B2 * | 9/2004 | Gatto et al. | 424/401 |
| 6,876,736 B2 * | 4/2005 | Lamy et al. | 379/211.01 |
| 2001/0006666 A1 | 7/2001 | Harbeck | |
| 2002/0018790 A1 | 2/2002 | Vatter et al. | |
| 2002/0086039 A1 | 7/2002 | Lee et al. | |
| 2002/0120241 A1 | 8/2002 | Tyrrell et al. | |
| 2002/0120242 A1 | 8/2002 | Tyrrell et al. | |
| 2002/0128615 A1 | 9/2002 | Tyrrell et al. | |
| 2002/0128621 A1 | 9/2002 | Kruchoski et al. | |
| 2002/0136755 A1 | 9/2002 | Tyrrell et al. | |
| 2003/0130635 A1 | 7/2003 | Tate et al. | |
| 2003/0130636 A1 | 7/2003 | Brock et al. | |

FOREIGN PATENT DOCUMENTS

| | | |
|---|---|---|
| CH | 423 673 | 11/1996 |
| DE | 35 36 318 A1 | 4/1987 |
| DE | 41 36 540 A1 | 5/1992 |
| EP | 0 212 870 B1 | 4/1992 |
| EP | 0 350 275 B1 | 2/1994 |
| EP | 0 613 675 A1 | 9/1994 |
| EP | 0 732 108 A2 | 9/1996 |
| EP | 0 797 968 A1 | 10/1997 |
| EP | 0 815 841 A1 | 1/1998 |
| EP | 0 875 233 A1 | 11/1998 |
| EP | 0 922 452 A1 | 6/1999 |
| EP | 0 922 456 A1 | 6/1999 |
| EP | 1 057 476 A1 | 12/2000 |
| EP | 0 808 151 B1 | 8/2001 |
| GB | 880276 | 10/1961 |
| GB | 884688 | 12/1961 |
| GB | 2 033 751 A | 5/1980 |
| GB | 2 311 727 A | 10/1997 |
| JP | 55-025430 A | 2/1980 |
| JP | 56-110611 A | 9/1981 |
| JP | 59-053409 A | 3/1984 |
| JP | 59-122420 A | 7/1984 |
| JP | 59-227816 A | 12/1984 |
| JP | 60-006759 A | 1/1985 |
| JP | 61-129117 A | 6/1986 |
| JP | 61-194014 A | 8/1986 |
| JP | 63-264413 A | 11/1988 |
| JP | 10-37070 A | 2/1998 |
| JP | 10-306039 A | 11/1998 |
| WO | WO 90/12555 A1 | 11/1990 |
| WO | WO 92/09289 A1 | 6/1992 |
| WO | WO 93/16670 A1 | 9/1993 |
| WO | WO 93/21878 A1 | 11/1993 |
| WO | WO 94/09757 A1 | 5/1994 |
| WO | WO 94/09796 A1 | 5/1994 |
| WO | WO 95/19190 A1 | 7/1995 |
| WO | WO 96/16681 A1 | 6/1996 |
| WO | WO 96/16682 A1 | 6/1996 |
| WO | WO 97/05908 A2 | 2/1997 |
| WO | WO 97/05909 A2 | 2/1997 |
| WO | WO 97/38735 A1 | 10/1997 |
| WO | WO 97/38738 A1 | 10/1997 |
| WO | WO 98/03147 A1 | 1/1998 |
| WO | WO 98/47546 A1 | 10/1998 |
| WO | WO 98/55159 A2 | 12/1998 |
| WO | WO 99/12530 A1 | 3/1999 |
| WO | WO 99/13861 A1 | 3/1999 |
| WO | WO 99/26610 A1 | 6/1999 |
| WO | WO 99/26618 A1 | 6/1999 |
| WO | WO 99/26619 A1 | 6/1999 |
| WO | WO 99/45771 A1 | 9/1999 |
| WO | WO 99/45973 A1 | 9/1999 |
| WO | WO 99/45974 A1 | 9/1999 |
| WO | WO 99/45976 A1 | 9/1999 |
| WO | WO 99/46316 A2 | 9/1999 |
| WO | WO 99/62478 A1 | 12/1999 |
| WO | WO 00/38747 A2 | 7/2000 |
| WO | WO 00/64407 A1 | 11/2000 |
| WO | WO 00/64501 A1 | 11/2000 |
| WO | WO 00/64503 A1 | 11/2000 |
| WO | WO 00/69481 A1 | 11/2000 |
| WO | WO 00/69482 A1 | 11/2000 |
| WO | WO 00/69483 A1 | 11/2000 |
| WO | WO 00/69484 A1 | 11/2000 |
| WO | WO 00/71177 A1 | 11/2000 |
| WO | WO 01/47455 A1 | 7/2001 |
| WO | WO 01/64156 A1 | 9/2001 |
| WO | WO 01/72262 A2 | 10/2001 |
| WO | WO 02/34305 A2 | 5/2002 |
| WO | WO 02/051456 A2 | 7/2002 |
| WO | WO 02/055119 A2 | 7/2002 |

OTHER PUBLICATIONS

Patent Abstracts of Japan 02053709 A: Description of Masaru et al., "Thixotropic Semi-Solid Composition."

Patent Abstracts of Japan 06065104 A: Description of Michio, "Powder Composition for Dermatic Application Prevented From Scatterability."

Patent Abstracts of Japan 07267839 A: Description of Yoshiko et al., "Ointment Composition Adhesive to Oral Mucosa."

Patent Abstracts of Japan 09151112 A: Description of Yasuhiro et al., "Microemulsion Composition."

American Society for Testing Materials (ASTM) Designation: D 1321—92, "Standard Test Method for Needle Penetration of Petroleum Waxes[1]", pp. 483-485, published Dec. 1992.

American Society for Testing Materials (ASTM) Designation: D 3236-88, "Standard Test Method for Apparent Viscosity of Hot Melt Adhesives and Coating Materials[1]", pp. 326-331, published Dec. 1988.

Federal Test Method Standard No. 191A, Method 5450, "Permeability to Air; Cloth; Calibrated Orifice Method", Jul. 20, 1978.

Federal Test Method Standard No. 191A, Method 5514, "Water Resistance of Cloth; Low Range, Hydrostatic Pressure Method", Jul. 20, 1978.

"Blue Moon Salves and Balms," Blue Moon Soaps: Herbal, Natural Bath Supplies and Gifts, Internet web page, "http://www.bluemoonsoaps.com/balm.html", viewed and printed Feb. 28, 2002, 2 pages.

"Snow Balm," Snow Pharmaceuticals, LLC, Internet web page, "http://www.snowbalm.com/intro.htm", viewed and printed Feb. 28, 2002, 3 pages.

"The Arbonne Baby Care," The White Whale, Internet web page, "http://thewhitewhale.com/babycare.htm", viewed and printed Feb. 28, 2002, 2 pages.

Akin, Frank J. et al., "A Refined Method to Evaluate Diapers for Effectiveness in Reducing Skin Hydration Using the Adult Forearm," *Skin Research and Technology*, 1997, pp. 173-176.

Barbero, Giulio J. et al., "Stool Trypsin and Chymotrypsin," *American Journal of Diseases of Children*, vol. 112, Jul. through Dec. 1966, pp. 536-540.

Barry, B.W. and A.J. Grace, "Investigation of Semisolid Lipophilic Preparations by Small Strain and Continuous Shear Viscometry and Their Application to Texture Profile," *Journal of Pharmaceutical Sciences*, vol. 60, No. 6, Jun. 1971, pp. 814-820.

Berg, Ronald W. et al., "Association of Skin Wetness and pH With Diaper Dermatitis," *Pediatric Dermatology*, vol. 11, No. 1, Mar. 1994, pp. 18-20.

Boylan, James C., "Rheological Study of Selected Pharmaceutical Semisolids," *Journal of Pharmaceutical Sciences*, vol. 55, No. 7, Jul. 1966, pp. 710-715.

Braudo, E.E. et al., "The Effect Produced by the Green Tea Components and Tannin on the Fermentative Activity of Trypsin in Vitro," *Vopr Pitan*, vol. 27, Issue No. 6, Nov.-Dec. 1968, pp. 40-44. (Russian with English summary).

Bremecker, K.D. et al., "Novel Concept for a Mucosal Adhesive Ointment," *Journal of Pharmaceutical Sciences*, vol. 73, No. 4, Apr. 1984, pp. 548-552.

Davies, Owen L. and Peter L. Goldsmith, editors, *Statistical Methods in Research and Production*, Fourth Revised Edition, published by Longman Inc., New York, 1984, p. 460.

Davis, S.S. et al., "Some Limitations of Continuous Shear Methods for the Study of Pharmaceutical Semi-Solids," *Journal of Pharmacy and Pharmacology*, vol. 20, Supplemental Issue, Dec. 1968, pp. 157S-167S.

Drechsler, Lee Ellen et al., "The Wipe: A Carrier of Skin Benefits," *Cosmetics & Toiletries*, vol. 116, No. 10, Oct. 2001, pp. 33-36, 38, 40, 42.

Eccleston, G.M. et al., "Correlation of Viscoelastic Functions for Pharmaceutical Semisolids: Comparison of Creep and Oscillatory Tests for Oil-in-Water Creams Stabilized by Mixed Emulsifiers," *Journal of Pharmaceutical Sciences*, No. 12, Dec. 1973, 1954-1961.

Eccleston, G.M., "Structure and Rheology of Cetomacrogol Creams: The Influence of Alcohol Chain Length and Homologue Composition," *Journal of Pharmacy and Pharmacology*, vol. 29, No. 3, Mar. 1977, pp. 157-162.

Eros, I. and A. Thaleb, "Rheological Studies of Creams: I. Rheological Functions and Structure of Creams," *Acta Pharmaceutica Hungarica*, vol. 64, No. 3, May 1994, pp. 101-103.

Fuhrer, C., "Gel Structure of Fatty Alcohols in Ointment Bases," *Pharmazie*, vol. 26, No. 1, Jan. 1971, pp. 43-45. (German).

Haverback, Bernard J. et al., "Measurement of Trypsin and Chymotrypsin in Stool: A Diagnostic Test for Pancreatic Exocrine Insuffieciency," *Gastroenterology*, vol. 44, 1963, pp. 588-597.

Huttenrauch, R., "Activation Energies in Plastic Deformation of Ointment Gels," *Pharmazie*, vol. 28, No. 4, Apr. 1973, 244-249. (German).

Imai, Satoshi and Chihiro Kuwabara, "Infant Skin and Its Care," *Cosmetics & Toiletries*, vol. 107, Jul. 1992, pp. 85,86,88-90.

Kedzierewicz, F. et al., "Preparation of Silicon Microspheres by Emulsion Polymerization: Application to the Encapsulation of a Hydrophilic Drug," *Journal of Microencapsulation*, 1998, pp. 227-236.

Muguet, V. et al., "Formulation of Shear Rate Sensitive Multiple Emulsions," *Journal of Controlled Release*, vol. 70, No. 1-2, Jan. 29, 2001, pp. 37-49.

Odio, Mauricio R. et al., "Continuous Topical Administration of a Petrolatum Formulation by a Novel Disposable Diaper. 1. Effect on Skin Surface Microtopography," *Dermatology*, 2000; 200(3):232-237.

Odio, Mauricio R. et al., "Continuous Topical Administration of a Petrolatum Formulation by a Novel Disposable Diaper. 2. Effect on Skin Condition," *Dermatology*, 2000; 200(3):238-243.

Pena, Lorraine E. et al., "Structural Rheology of a Model Ointment," *Pharmaceutical Research*, vol. 11, No. 6, Jun. 1994, pp. 875-881.

Popovici, Iuliana et al., "The Physico-Chemical Characterization and Therapeutical Evaluation of Cicatrol," *Revista Medico-Chirurgicala Societatii de Medici si Naturalisti din Iasi*, vol. 96, No. 1-2, Jan.-Jun. 1992, pp. 57-64.

Preston, Sandra L. and Bobby G. Bryant, "Etiology and Treatment of Diaper Dermatitis," *Hospital Pharmacy*, vol. 29, No. 12, Dec. 1994, pp. 1086-1088, 1097.

Salo, D.P. et al., "Ion Exchange Properties of Clay Minerals and Its Use for Obtaining Clays With Planned Properties. 3. Effect of the Nature of Exchange Kation on the Structure-Mechanical Properties of Suspensions and Ointment Bases Prepared From Clays of Montmorillonite and Sepiolite-Mountain Leather Groups," *Farm Zh*, vol. 23, No. 6, 1968, pp. 61-66 (Ukrainian).

Sires, Ulrike I. and Susan B. Mallory, "Diaper Dermatitis—How to Treat and Prevent," *Postgraduate Medicine*, vol. 98, No. 6, Dec. 1995, pp. 79-82, 84, 86.

Taleb, A. and I. Eros, "Rheological Studies of Creams. II. Effect of Water Content on Rheological Characteristics," *Acta Pharmaceutica Hungarica*, vol. 66, No. 2, Mar. 1996, pp. 71-76.

Tamburic, S. et al., "An Investigation Into the Use of Thermorheology and Texture Analysis in the Evaluation of W/O Creams Stabilized With a Silicone Emulsifier," *Pharmaceutical Development Technology*, vol. 1, No. 3, Oct. 1996, pp. 299-306.

Vinson, Joe and John Proch, "Inhibition of Moisture Penetration to the Skin by a Novel Incontinence Barrier Product," *Journal of Wound, Ostomy and Continence Nursing*, vol. 25, No. 5, Sep. 1998, pp. 256-260.

Zielinski, Ruth, and Elizabeth Hanson; "Diaper Dermatitis: Medical Aspects of Skin Care," *Nonwovens World*, Feb.-Mar. 2000, pp. 60-65.

Safarik, Ivo, "Isolation of Trypsin By Column Chromatography on Tea Particles," *Journal of Chromatography*, 315, Elsevier Science Publishers B.V., Amsterdam, The Netherlands, 1984, pp. 478-480.

\* cited by examiner

ABSORBENT ARTICLES WITH COMPOSITIONS FOR REDUCING IRRITATION RESPONSE

This patent application is a continuation-in-part of application Ser. No. 09/747,382 entitled "Absorbent Articles With Non-Aqueous Compositions Containing Botanicals" filed in the U.S. Patent and Trademark Office on Dec. 22, 2000 now U.S. Pat. No. 6,749,860; and of application Ser. No. 09/746,888 entitled "Absorbent Articles With Hydrophilic Compositions Containing Botanicals" filed in the U.S. Patent and Trademark Office on Dec. 22, 2000. The entirety of application Ser. Nos. 09/747,382 and 09/746,888 are hereby incorporated by reference.

BACKGROUND OF THE INVENTION

The present invention relates generally to the inclusion of skin care compositions that contain botanical compounds on the bodyfacing materials of disposable absorbent articles, such as diapers, training pants, adult incontinence products, underpants, feminine care products, nursing pads, wound dressings and similar articles having absorbent capacity. The skin care compositions are capable of mitigating the irritation response of the skin of wearers of such articles and inhibiting the activity of deleterious enzymes.

The stratum corneum is the outer-most layer of the skin and is responsible for regulating skin water levels and functioning as a barrier against chemicals and other stress agents found in the environment. The complex arrangement of lipids in the intercellular space of the stratum corneum is responsible for the establishment of normal barrier function. Multi-layered structures of cholesterol, ceramides and fatty acids, as well as some other minor lipids, provide the major barrier to the transport of substances into or through the skin. The overall structure of the stratum corneum acts as the frontline barrier to the skin.

Skin health and protection from biological insults are important for wearers of absorbent articles. Absorbent articles such as diapers, training pants, incontinence products and feminine care products are worn such that they are in direct contact with the skin of the wearer. An unavoidable consequence of the use of absorbent articles is that the skin is exposed more directly to various physical and biological insults. Consequently, the barrier function of the skin covered by the absorbent article is put at risk. In order to provide disposability, absorbent articles are primarily constructed of nonwoven materials. Even though nonwoven materials are engineered to have soft hand and drape, they rub against the skin and there is friction. Such friction constitutes one form of physical insult to the skin barrier. Friction against the skin barrier also occurs with the use of absorbent tissues and wipes. Absorbent tissue and wipe products are frequently used for cleansing the skin areas covered by absorbent articles. Absorbent tissue and wipe products are necessary for removing biological waste materials from the skin.

In addition to these physical insults, skin covered by absorbent articles is also frequently exposed to biological insults. Biological fluids, such as urine, feces, vaginal secretions and nasal secretions, may contain a variety of components that can damage the skin barrier. Examples of these components include proteases, lipases and bile acids. Once the skin barrier is compromised, these components, in addition to other constituents of biological fluids, can initiate or exacerbate inflammation of the skin.

Diaper dermatitis is a genre of skin conditions that, in large part, originate from impaired skin barrier function. Impairment of the skin barrier can result from a variety of factors, including: increased skin hydration due to the occlusion of the skin caused by diapers, enzymatic skin damage due to fecal and urinary enzymes, and physical damage caused by friction against the diaper surface and repeated cleaning of the skin with absorbent tissues or wet wipes.

Excessive hydration of the skin also has a negative effect on the skin barrier. The hydration level of diapered skin, for example, may reach between five to ten times that of undiapered skin. Frequent contact of diapered skin with urine may also contribute to increased skin hydration. Increased skin hydration disrupts skin lipid organization in the stratum corneum. This disruption may increase the permeability of the skin to irritants from feces and urine, thus increasing the risk of skin inflammation.

Disposable absorbent articles such as diapers, training pants, adult incontinence products, absorbent under pants, feminine care products and nursing pads have been used to absorb body fluids and leave the skin dry. Disposable absorbent articles of this type generally include a liquid impermeable backsheet member, an absorbent core or assembly, and a liquid permeable body facing or liner material. The body facing or liner material comes into contact with the wearer's skin. While the body facing material is made of a soft, compliant material, the material rubs against the skin during use and may not leave the skin completely dry and free of the bodily fluids, such as solid or semi-solid waste, the absorbent article is trying to absorb. During frequent insults of bodily fluids and frequent use of disposable absorbent articles, the skin can become irritated and appear red and be sore to the touch.

Creams, lotions or ointments can be used to provide an artificial hydrophobic barrier on the skin and to treat skin conditions such as diaper rash. Application of these types of products to the skin is often messy and inconvenient. Often, these products are not used prophylactically and are only used when signs of diaper rash are visible.

Diaper liners and other bodyfacing materials may be treated with emollients, such as petrolatum, that can be transferred to the skin through normal diapering practices. Once transferred to the skin, diaper liner formulations may provide an artificial barrier against feces and urine. These formulations may require high concentrations of petrolatum to ensure sufficient transfer to the skin to provide a benefit. High concentrations of petrolatum can be messy, greasy to the touch, and may impair the fluid handling properties of an absorbent article, such as a diaper. The greasy consistency of petrolatum can lead to smearing of the agent over the skin and onto clothes and other materials.

Formulations, such as those containing petrolatum, are applied to the bodyfacing materials of absorbent articles during manufacture. In order to process and apply the formulations to the bodyfacing materials, the formulations need to be in a semi-solid or fluid state. However, in order to have stability on the bodyfacing material after manufacture, the formulations need to be semi-solid or solid across a wide range of shipping and storage temperatures. Not all of the presently known formulations are sufficiently stable on the bodyfacing materials. Consequently, such formulations may transfer off of the bodyfacing material prematurely or the formulations may migrate away from the skin-facing surfaces of the materials.

Thus, what is needed is a topically effective composition delivered from a bodyside or bodyfacing material of an absorbent article that protects, maintains, recovers or otherwise benefits skin barrier function against physical damage and irritants in biological fluids. It would also be desirable to provide a topical composition delivered from a bodyside material of an absorbent article that absorbs into the outer layers of the skin, is non-greasy and non-occlusive and cosmetically acceptable to the consumer. Additionally, it would be desirable to provide a topical composition having improved stability on the bodyside material of an absorbent article. Further, it would be desirable to provide a topical composition delivered from a bodyside material of an absorbent article that does not impair the waste containment functions of the absorbent article.

SUMMARY OF THE INVENTION

In response to the difficulties and problems discussed above, compositions and the use of those compositions on absorbent articles for inhibiting enzyme activity and subduing the inflammatory response of the skin have been discovered. The compositions of the invention provide several benefits to skin including inhibiting the activity of enzymes that are deleterious to the skin and subduing the skin's inflammatory response. While the compositions of the inventions can have a variety of applications, the compositions are particularly beneficial when used in conjunction with absorbent articles such as diapers, incontinence garments, feminine care products, training pants, diaper pants, nursing pads and wound dressings. Additionally, the compositions of the invention could also provide benefits when used in conjunction with tissue, pre-moistened wipe products and cosmetic cleansing and buffing pads. A further benefit of the compositions of the invention is that the compositions show improved stability during processing and application to an article. The purposes and advantages of the present invention will be set forth in and apparent from the description that follows, as well as will be learned by practice of the invention. Additional advantages of the invention will be realized and attained by the compositions and articles particularly pointed out in the written description and claims hereof, as well as from the appended drawings.

In one aspect, the present invention relates to an absorbent article that includes an outer cover, a bodyside liner, an absorbent body and a composition. The bodyside liner is typically liquid permeable and defines a bodyfacing surface. The bodyside liner is connected in a generally superposed relation to the outer cover. The absorbent body is located between the bodyside liner and the outer cover. The composition is on a portion or the entire bodyfacing surface of the bodyside liner. The composition can be generally solid or semi-solid. The composition includes from about 10 to about 90 weight percent of a hydrophilic solvent, from about 5 to about 90 percent by weight of a high molecular weight polyethylene glycol, from about 0 to about 40 percent by weight of a $C_{14}$ to $C_{30}$ fatty alcohol, from about 0 to about 40 percent by weight of a $C_{14}$ to $C_{30}$ fatty acid and from about 0.1 to about 15 percent by weight of extracted botanical active. The extracted botanical active may be selected from grape seed, green tea, constituents of grape seed and green tea and mixtures of such actives. The extracted botanical active has a BAPNA-Trypsin Inhibition ($IC_{50} \times 10^{-3}$) of from about 0.01 to about 500 as measured by the BAPNA-Trypsin Inhibition Test that is described in this specification. In another aspect, the BAPNA-Trypsin Inhibition of the extracted botanical active is from about 0.01 to about 200. Additionally, the BAPNA-Trypsin Inhibition of the extracted botanical active may be from about 0.01 to about 100 or it may be from about 0.01 to about 10. In yet another aspect of the invention, the BAPNA-Trypsin Inhibition of the extracted botanical active is from about 0.01 to about 1.

The hydrophilic solvent of the composition may be selected from water, propylene glycol, low molecular weight polyethylene glycol, glycerin, hydrogenated starch hydrolysate, methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, sorbitol, silicone glycols and mixtures thereof. For the high molecular weight polyethylene glycol of the composition, the molecular weight is from about 720 to about 1,840,000 daltons. The fatty alcohol of the composition may be selected from cetyl alcohol, stearyl alcohol, arachidyl alcohol, behenyl alcohol and mixtures thereof.

The composition may further include from about 0.1 to about 20 percent by weight of one or more viscosity enhancers. The viscosity enhancer of the composition may be selected from actrylamides copolymers, agar, gelatin, water dispersible metal soaps, butoxy chitosan, carboxymethyl cellulose, hydrated silica, kelp, magnesium silicate, alumina magnesium silicate, smectite, organomodified clays, methyl cellulose, PEG crosspolymer, polyvinyl alcohols, sodium acrylates copolymers, partially crosslinked polyacrylic acid polymers, TEA alginates, xanthan gums, yeast polysaccharides and mixtures thereof. The composition may also include from about 1 to about 10 percent by weight of emulsifying surfactant having a combined HLB in a range greater than 7. The emulsifying surfactant may be selected from glyceryl stearate SE, glycol stearate SE, water dispersible metal soaps, polysorbate 20, polysorbate 40, polysorbate 60, polysorbate 80 and mixtures thereof. Additionally, the composition may include from about 0.1 to about 30 percent by weight of one or more natural fats or oils selected from Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Benenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

The composition may also include from about 0.1 to about 10 percent by weight of one or more sterols or sterol derivatives selected from cholesterol, sitosterol, stigmasterol, and ergosterol, as well as, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, sterol esters and mixtures thereof. Additionally, the composition may include from about 0.1 to about 10 percent by weight of one or more emollients selected from petroleum based oils, petrolatum, mineral oils, alkyl dimethicones, alkyl methicones, phenyl silicones, alkyl trimethylsilanes, dimethicone, lanolin, fatty alcohols and mixtures thereof. Further, the composition may include from about 0.5 to about 10 percent by weight of one or more rheology modifiers selected from natural clays, synthetic analogs of natural clays, alginates, natural gums and mixtures thereof.

In another aspect of the invention, the composition on at least a portion of the bodyfacing surface of the bodyside liner includes from about 50 to about 95 percent by weight of emollient, from about 1 to about 40 percent by weight of viscosity enhancer and from about 0.1 to about 15 percent by weight of extracted botanical active wherein the extracted botanical active is selected from grape seed, green tea, constituents of grape seed and green tea and mixtures of these actives. The emollient of the composition may be selected from petrolatum, vegetable based oils, mineral oils, dimethicone, lanolin, glycerol esters, alkoxylated carboxylic acids, alkoxylated alcohols, fatty alcohols and mixtures thereof. The viscosity enhancer of the composition may be selected from polyolefin resins, lipophilic/oil thickeners, ethylene/vinyl acetate copolymers, organically modified clays, polyethylene, silica, silica silylate, silica methyl silylate, colloidal silicone dioxide, alkyl hydroxy ethyl cellulose, microcrystalline wax, shellac wax, hexadecyl cosanyl hexacosanate, $C_{20}$-$C_{40}$ alkyl hydroxystearyl stearate, glycol montanate, ozokerite wax, polyperfluoromethylisopropylether montan wax and mixtures thereof.

This composition may also include from about 5 to about 48 percent by weight of one or more solidifying agents selected from beeswax, behenyl behenate, behenyl benzoate, branched esters, candelilla wax, carnauba wax, synthetic carnauba wax, PEG-12 carnauba wax, cerasin, microcrystalline wax, hydrogenated microcrystalline wax, hexadecylcosanyl hexacosanate, polyperfluoromethylisopropylether montan wax, alkylmethylsiloxanes, glycol montanate, jojoba wax, lanolin wax, ozokerite, paraffin, synthetic paraffin, polyethylene, $C_{20}$-$C_{40}$ alkyl hydroxystearyl stearate, $C_{30}$ alkyl dimethicone, cetyl esters, zinc stearate, shellac wax, hydrogenated cottonseed oil, hydrogenated squalene, hydrogenated jojoba oil and mixtures thereof. The composition may also include from about 0.1 to about 48 percent by weight of one or more natural fats or oils selected from Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Benenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

Additionally, the composition may include from about 0.1 to about 10 percent by weight of one or more sterols or sterol derivatives selected from cholesterol, sitosterol, stigmasterol, and ergosterol, as well as, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, sterol esters and mixtures thereof. Further, the composition may include from about 0.5 to about 20 percent by weight of one or more rheology modifiers selected from silica, silica silylate, silica methyl silylate, quaternary starch compounds, quaternary modified clays, organically modified clays and mixtures thereof. The composition may also include from about 1 to about 20 percent by weight of one or more clays selected from natural clays, synthetic analogs of natural clays and mixtures thereof.

The absorbent articles of the invention advantageously protect the skin in such a way not observed with conventional absorbent articles and compositions applied to absorbent articles. Consequently, use of absorbent articles having compositions of the invention protects the skin from mechanical damage and biological irritation. It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles of the invention. Together with the description, the drawings serve to explain the various aspects of the invention.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the claims. Like parts of the absorbent articles depicted in the drawings are referred to by the same reference numerals.

DETAILED DESCRIPTION OF THE INVENTION

The present invention is directed to solving problems related to protecting the barrier function of the skin when the skin is exposed to causes of physical and biological damage. Similarly, the present invention is directed to solving problems related to the prevention and treatment of diaper rash.

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The present invention encompasses compositions as they are applied to the bodyfacing materials of absorbent articles and absorbent articles including compositions. The following detailed description will be made in the context of one type of absorbent article, a disposable diaper that is adapted to be worn by infants about their lower torso. It is readily apparent, however, that the absorbent article of the present invention would also be suitable for use as another type of absorbent article, such as a feminine care pad, an incontinence garment, a training pant, a prefastened or refastenable diaper pant, a wound dressing or a nursing pad.

Figure 1:
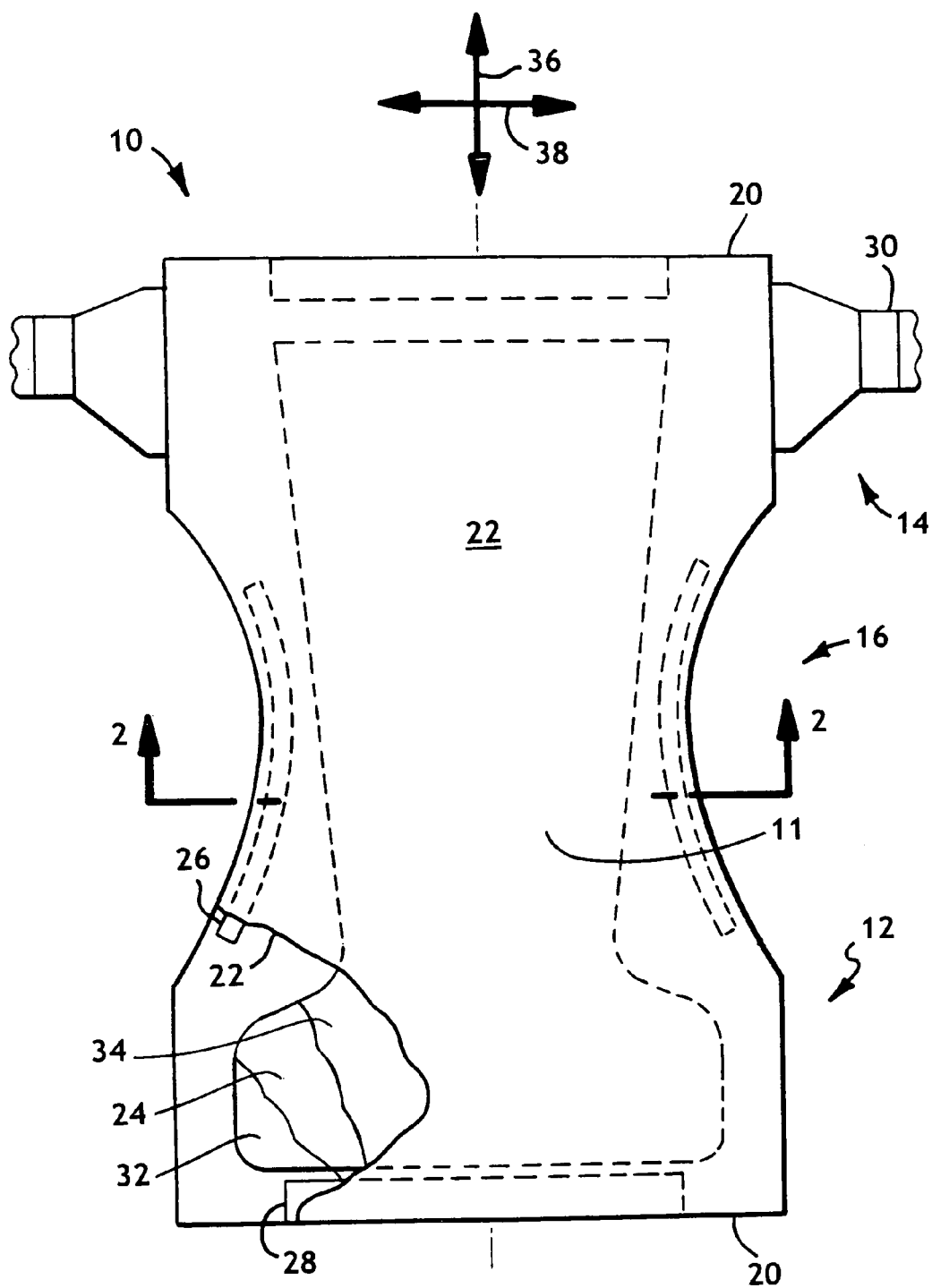
FIG. 1 representatively shows a partially cut away, top plan view of an absorbent article according to one aspect of the invention in a stretched and laid flat condition with the surface of the article that contacts the skin of the wearer facing the viewer.

FIG. 1 is a representative plan view of a disposable diaper 10 of the present invention in a flat-out, uncontracted state (i.e., with all elastic induced gathering and contraction removed). The bodyfacing surface 11 of the diaper 10, that is, the surface 11 of the diaper 10 that contacts the wearer is facing the viewer. The compositions of the invention can be applied to one or more bodyfacing materials that are components of the diaper 10. As used herein, the term 'bodyfacing material' includes, but is not limited to, materials such as the bodyside liner or topsheet, elastic material, tissue, intake and distribution material and absorbent material. Each of these materials and components of a diaper 10 are described more fully herein. The compositions of the invention are applied to one or more of the bodyfacing materials in order to have a beneficial effect on the skin barrier. The bodyfacing material of the present invention can be a single layer or multi-layered.

With reference to FIG. 1, the diaper 10 generally defines a front waist section 12, a rear waist section 14, and an intermediate section 16 that interconnects the front and rear waist sections 12 and 14. The front and rear waist sections 12 and 14 include the general portions of the diaper 10 that are constructed to extend substantially over the wearer's front and rear abdominal regions, respectively, during use. The intermediate section 16 of the diaper 10 includes the general portion of the diaper 10 that is constructed to extend through the wearer's crotch region between the legs.

The diaper 10 includes a vapor permeable backsheet or outer cover 20, a liquid permeable topsheet or bodyside liner 22 positioned in facing relation with the outer cover 20, and an absorbent body 24, such as an absorbent pad, which is located between the outer cover 20 and the bodyside liner 22. The outer cover 20 defines a length and a width that, in the illustrated aspect, coincide with the length and width of the diaper 10. The absorbent body 24 generally defines a length and width that are less than the length and width of the outer cover 20, respectively. Thus, marginal portions of the diaper 10, such as marginal sections of the outer cover 20, may extend past the terminal edges of the absorbent body 24. In the illustrated aspects, for example, the outer cover 20 extends outwardly beyond the terminal marginal edges of the absorbent body 24 to form side margins and end margins of the diaper 10. The bodyside liner 22 is generally coextensive with the outer cover 20 but may optionally cover an area that is larger or smaller than the area of the outer cover 20, as desired. In other words, the bodyside liner 22 is connected in superposed relation to the outer cover 20. The outer cover 20 and bodyside liner 22 are intended to face the garment and body of the wearer, respectively, while in use.

To provide improved fit and to help reduce leakage of body exudates from the diaper 10, the diaper side margins and end margins may be elasticized with suitable elastic members, such as single or multiple strands of elastic. The elastic strands may be composed of natural or synthetic rubber and may optionally be heat shrinkable or heat elasticizable. For example, as representatively illustrated in FIG. 1, the diaper 10 may include leg elastics 26 that are constructed to operably gather and shirr the side margins of the diaper 10 to provide elasticized leg bands which can closely fit around the legs of the wearer to reduce leakage and provide improved comfort and appearance. Similarly, waist elastics 28 can be employed to elasticize the end margins of the diaper 10 to provide elasticized waists. The waist elastics 28 are configured to operably gather and shirr the waist sections to provide a resilient, comfortably close fit around the waist of the wearer. In the illustrated aspects, the elastic members are illustrated in their uncontracted, stretched condition for the purpose of clarity.

Fastening means, such as hook and loop fasteners 30, are employed to secure the diaper 10 on a wearer. Alternatively, other fastening means, such as buttons, pins, snaps, adhesive tape fasteners, cohesives, mushroom-and-loop fasteners, or the like, may be employed. Additionally, more than two fasteners can be provided, particularly if the diaper 10 is to be provided in a prefastened configuration. The fasteners can vary in size and form.

The diaper 10 may further include other layers between the absorbent body 24 and the bodyside liner 22 or outer cover 20. For example, as representatively illustrated in FIGS. 1 and 2, the diaper 10 may include a ventilation layer 32 located between the absorbent body 24 and the outer cover 20 to insulate the outer cover 20 from the absorbent body 24, to improve air circulation and to effectively reduce the dampness of the garment facing surface of the outer cover 20. The ventilation layer 32 may also assist in distributing fluid exudates to portions of the absorbent body 24 that do not directly receive the insult. The diaper 10 may also include a surge management layer 34 located between the bodyside liner 22 and the absorbent body 24 to prevent pooling of the fluid exudates and further improve air exchange and distribution of the fluid exudates within the diaper 10.

The diaper 10 may be of various suitable shapes. For example, the diaper may have an overall rectangular shape, T-shape or an approximately hourglass shape. In the shown aspect, the diaper 10 has a generally I-shape. The diaper 10 further defines a longitudinal direction 36 and a lateral direction 38. Other suitable diaper components that may be incorporated on absorbent articles of the present invention include containment flaps, waist flaps, elastomeric side panels, and the like which are generally known to those skilled in the art. Likewise, if the diaper 10 is to be sold in a prefastened condition, the diaper 10 may have passive bonds (not shown) that join the rear waist section 14 with the front waist section 12.

Examples of diaper configurations suitable for use in connection with the instant application that may include other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,192,606 issued Mar. 9, 1993, to Proxmire et al., and U.S. Pat. No. 5,509,915 issued Apr. 23, 1996 to Hanson et al., the disclosures of which are herein incorporated by reference.

The various components of the diaper 10 are integrally assembled together employing various types of suitable attachment means, such as adhesive, sonic bonds, thermal bonds or combinations thereof. In the shown aspect, for example, the bodyside liner 22 and outer cover 20 are assembled to each other and to the absorbent body 24 with lines of adhesive, such as a hot melt, pressure-sensitive adhesive. Similarly, other diaper components, such as the elastic members 26 and 28, fastening members 30, and ventilation and surge layers 32 and 34 may be assembled into the diaper 10 by employing the above-identified attachment mechanisms.

The outer cover 20 of the diaper 10, as representatively illustrated in FIG. 1, is composed of a substantially vapor permeable material. The permeability of the outer cover 20 is configured to enhance the breathability of the diaper 10 and to reduce the hydration of the wearer's skin during use without allowing excessive condensation of vapor, such as urine, on the garment facing surface of the outer cover 20 that can undesirably dampen the wearer's clothes. The outer cover 20 is generally constructed to be permeable to at least water vapor and has a water vapor transmission rate of at least about 1000 g/m$^2$/24 hr, where the water vapor transmission rate test is described in PCT Publication WO 02/051456 published on Jul. 4, 2002. For example, the outer cover 20 may define a water vapor transmission rate of from about 1000 to about 6000 g/m$^2$/24 hr. Materials that have a water vapor transmission rate less than those above do not allow a sufficient amount of air exchange and undesirably result in increased levels of skin hydration.

The outer cover 20 is also desirably substantially liquid impermeable. For example, the outer cover 20 may be constructed to provide a hydrohead value of at least about 60 cm, desirably at least about 80 cm, and more desirably at least about 100 cm when subjected to the Hydrostatic Pressure Test described in PCT Publication WO 02/051456 published on Jul. 4, 2002. Materials that have hydrohead values less than those above undesirably result in the strike through of liquids, such as urine, during use. Such fluid strike through can undesirably result in a damp, clammy feeling on the outer cover 20 during use.

The outer cover 20 may be composed of any suitable materials that either directly provide the above desired levels of liquid impermeability and air permeability or, in the alternative, materials that can be modified or treated in some manner to provide such levels. In one aspect, the outer cover 20 may be a nonwoven fibrous web constructed to provide the required level of liquid impermeability. For example, a nonwoven web composed of spunbond or meltblown polymer fibers may be selectively treated with a water repellent coating or laminated with a liquid impermeable, vapor permeable polymer film to provide the outer cover 20. In a particular aspect of the invention, the outer cover 20 may include a nonwoven web composed of a plurality of randomly deposited hydrophobic thermoplastic meltblown fibers that are sufficiently bonded or otherwise connected to one another to provide a substantially vapor permeable and substantially liquid impermeable web. The outer cover 20 may also include a vapor permeable nonwoven layer that has been partially coated or otherwise configured to provide liquid impermeability in selected areas.

Examples of suitable materials for the outer cover 20 are also described in U.S. Pat. No. 5,482,765 issued Jan. 9, 1996 in the name of Bradley et al. and entitled "NONWOVEN FABRIC LAMINATE WITH ENHANCED BARRIER PROPERTIES"; U.S. Pat. No. 5,879,341 issued Mar. 9, 1999 in the name of Odorzynski et al. and entitled "ABSORBENT ARTICLE HAVING A BREATHABILITY GRADIENT"; U.S. Pat. No. 5,843,056 issued Dec. 1, 1998, in the name of Good et al. and entitled "ABSORBENT ARTICLE HAVING A COMPOSITE BREATHABLE BACKSHEET"; and U.S. Pat. No. 6,075,179 issued Jun. 13, 2000, in the name of McCormack et al. and entitled "LOW GAUGE FILMS AND FILM/NONWOVEN LAMINATES", the disclosures of which are herein incorporated by reference.

In another aspect, the outer cover 20 is provided by an extensible material. Further, the outer cover 20 can also be provided by a material having stretch in both the longitudinal 36 and lateral 38 directions. When the outer cover 20 is made from extensible or stretchable materials, the diaper 10 provides additional benefits to the wearer including improved fit. Examples of absorbent articles including extensible outer covers are described in U.S. Pat. No. 6,503,236 issued Jan. 7, 2003, in the name of Uitenbroek et al. and entitled "ABSORBENT ARTICLE HAVING AN EXTENSIBLE OUTER COVER WITH ACTIVATABLE ZONED BREATHABILITY", the disclosure of which is herein incorporated by reference.

Figure 2:
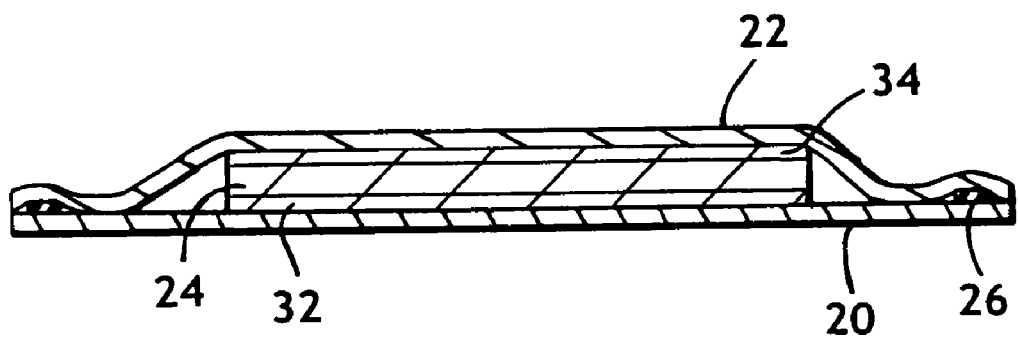
FIG. 2 representatively shows a sectional view of the absorbent article of FIG. 1 taken along line 2-2.

The bodyside liner 22, as representatively illustrated in FIGS. 1 and 2, defines a bodyfacing surface 11 that is compliant, soft feeling, and nonirritating to the wearer's skin. Further, the bodyside liner 22 may be less hydrophilic than the absorbent body 24, to present a relatively dry surface to the wearer, and may be sufficiently porous to be liquid permeable, permitting liquid to readily penetrate through its thickness. A suitable bodyside liner 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 22 is suitably employed to help isolate the wearer's skin from liquids held in the absorbent body 24.

Various woven and nonwoven fabrics can be used for the bodyside liner 22. For example, the bodyside liner 22 may be composed of a meltblown or spunbond web of polyolefin fibers. The bodyside liner 22 may also be a bonded-carded web composed of natural and/or synthetic fibers. The bodyside liner 22 may be composed of a substantially hydrophobic material, and the hydrophobic material may, optionally, be treated with a surfactant or otherwise processed to impart a desired level of wettability and hydrophilicity. In a particular aspect of the present invention, the bodyside liner 22 comprises a nonwoven, spunbond, polypropylene fabric composed of about 2.8-3.2 denier fibers formed into a web having a basis weight of about 22 grams per square meter and a density of about 0.06 gram per cubic centimeter.

In a particular aspect of the present invention, the bodyside liner 22 may be surface treated with about 0.3 weight percent of a surfactant mixture that contains a mixture of AHCOVEL Base N-62 surfactant and GLUCOPON 220UP surfactant in about a 3:1 ratio based on a total weight of the surfactant mixture. The AHCOVEL Base N-62 surfactant is purchased from Hodgson Textile Chemicals Inc., a business having offices in Mount Holly, N.C., and includes a blend of hydrogenated ethoxylated castor oil and sorbitan monooleate in a 55:45 weight ratio. The GLUCOPON 220UP surfactant is purchased from Henkel Corporation and includes alkyl polyglycoside. The surfactant may also include additional ingredients such as aloe. The surfactant may be applied by any conventional means, such as spraying, printing, brush coating, foam or the like. The surfactant may be applied to the entire bodyside liner 22 or may be selectively applied to particular sections of the bodyside liner 22, such as the medial section along the longitudinal centerline of the diaper, to provide greater wettability of such sections.

The absorbent body 24 of the diaper 10, as representatively illustrated in FIG. 1, may suitably comprise a matrix of hydrophilic fibers, such as a web of cellulosic fluff, mixed with particles of a high-absorbency material commonly known as superabsorbent material. In a particular aspect, the absorbent body 24 includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent body 24 may include a laminate of fibrous webs and superabsorbent material or other suitable matrix for maintaining a superabsorbent material in a localized area.

The absorbent body 24 may have any of a number of shapes. For example, the absorbent body 24 may be rectangular, I-shaped, or T-shaped. It is generally preferred that the absorbent body 24 is narrower in the intermediate section than in the front or rear waist sections of the diaper 10. The absorbent body 24 may be provided by a single layer or, in the alternative, may be provided by multiple layers, all of which need not extend the entire length and width of the absorbent body 24. In a particular aspect of the invention, the absorbent body 24 can be generally T-shaped with the laterally extending cross-bar of the "T" generally corresponding to the front waist section 12 of the absorbent article for improved performance, especially for male infants. In the illustrated aspects, for example, the absorbent body 24 across the front waist section 12 of the article has a cross-directional width of about 18 centimeters, the narrowest portion of the intermediate section 16 has a width of about 7.5 centimeters and in the rear waist section 14 has a width of about 11.4 centimeters.

The size and the absorbent capacity of absorbent body 24 should be compatible with the size of the intended wearer and the liquid loading imparted by the intended use of the absorbent article. Further, the size and the absorbent capacity of the absorbent body 24 can be varied to accommodate wearers ranging from infants through adults. In addition, it has been found that with the present invention, the densities and/or basis weights of the absorbent body 24 can be varied. In a particular aspect of the invention, the absorbent body 24 has an absorbent capacity of at least about 300 grams of synthetic urine.

In aspects wherein the absorbent body 24 includes the combination of hydrophilic fibers and high-absorbency particles, the hydrophilic fibers and high-absorbency particles can form an average basis weight for the absorbent body 24 that is within the range of about 400-900 grams per square meter. In certain aspects of the invention, the average composite basis weight of such an absorbent body 24 is within the range of about 500-800 grams per square meter, and preferably is within the range of about 550-750 grams per square meter to provide the desired performance.

To provide the desired thinness dimension to the various configurations of the absorbent article of the invention, the absorbent body 24 can be configured with a bulk thickness that is not more than about 0.6 centimeters. Preferably, the bulk thickness is not more than about 0.53 centimeters, and more preferably is not more than about 0.5 centimeters to provide improved benefits. The bulk thickness is determined under a restraining pressure of 0.2 psi (1.38 kPa).

The high-absorbency material can be selected from natural, synthetic, and modified natural polymers and materials. The high-absorbency materials can be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent body 24 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. In general, the high absorbency material is present in the absorbent body 24 in an amount of from about 5 to about 90 percent by weight, desirably in an amount of at least about 30 percent by weight, and even more desirably in an amount of at least about 50 percent by weight based on a total weight of the absorbent body 24. For example, in a particular aspect, the absorbent body 24 may include a laminate which includes at least about 50 percent by weight and desirably at least about 70 percent by weight of high-absorbency material overwrapped by a fibrous web or other suitable material for maintaining the high-absorbency material in a localized area.

An example of high-absorbency material suitable for use in the present invention is DRYTECH 2035 polymer available from Dow Chemical, a business having offices in Midland, Mich. Other suitable superabsorbents may include FAVOR SXM 880 polymer obtained from Stockhausen, a business having offices in Greensboro, N.C.

Optionally, a substantially hydrophilic tissue wrapsheet (not illustrated) may be employed to help maintain the integrity of the structure of the absorbent body 24. The tissue wrapsheet is typically placed about the absorbent body 24 over at least the two major facing surfaces thereof. The tissue wrapsheet can be composed of an absorbent cellulosic material, such as creped wadding or a high wet-strength tissue. In one aspect of the invention, the tissue wrapsheet can be configured to provide a wicking layer that helps to rapidly distribute liquid over the mass of absorbent fibers constituting the absorbent body 24.

Due to the thinness of absorbent body 24 and the high absorbency material within the absorbent body 24, the liquid uptake rates of the absorbent body 24, by itself, may be too low, or may not be adequately sustained over multiple insults of liquid into the absorbent body 24. To improve the overall liquid uptake and air exchange, the diaper 10 of the different aspects of the present invention may further include a porous, liquid-permeable layer of surge management material 34, as representatively illustrated in FIG. 1. The surge management layer 34 is typically less hydrophilic than the absorbent body 24, and has an operable level of density and basis weight to quickly collect and temporarily hold liquid surges, to transport the liquid from its initial entrance point and to substantially completely release the liquid to other parts of the absorbent body 24. This configuration can help prevent the liquid from pooling and collecting on the portion of the diaper 10 positioned against the wearer's skin, thereby reducing the feeling of wetness by the wearer. The structure of the surge management layer 34 also generally enhances the air exchange within the diaper 10.

Various woven and nonwoven fabrics can be used to construct the surge management layer 34. For example, the surge management layer 34 may be a layer composed of a meltblown or spunbond web of synthetic fibers, such as polyolefin fibers. The surge management layer 34 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 34 may be composed of a substantially hydrophobic material, and the hydrophobic material may optionally be treated with a surfactant or otherwise processed to impart a desired level of wettability and hydrophilicity. In a particular aspect, the surge management layer 34 includes a hydrophobic, nonwoven material having a basis weight of from about 30 to about 120 grams per square meter.

Additional materials suitable for the surge management layer 34 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference.

As representatively illustrated in FIG. 1, the diaper 10 may also include a ventilation layer 32 located between the outer cover 20 and the absorbent body 24. The ventilation layer 32 serves to facilitate the movement of air within and through the diaper 10 and prevent the outer cover 20 from being in surface to surface contact with at least a portion of the absorbent body 24. Specifically, the ventilation layer 32 serves as a conduit through which air and water vapor can move from the absorbent body 24 through the vapor permeable outer cover 20.

The ventilation layer 32 may be formed from materials described above as being suitable for the surge management layer 34 such as nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The ventilation layer 32 may also be formed from a porous foam material such as an open-celled polyolefin foam, a reticulated polyurethane foam, and the like. The ventilation layer 32 may include a single layer of material or a composite of two or more layers of material. In a particular aspect, the ventilation layer 32 includes a hydrophobic, nonwoven material having a thickness of at least about 0.10 centimeters determined under a restraining pressure of 0.05 psi (0.34 kPa) and a basis weight of from about 20 to about 120 grams per square meter. For example, the ventilation layer 32 may comprise a bonded-carded-web, nonwoven fabric that includes bicomponent fibers and that defines an overall basis weight of about 83 grams per square meter. The ventilation layer 32 in such a configuration can be a homogeneous blend composed of about 60 weight percent polyethylene/polyester (PE/PET), sheath-core bicomponent fibers that have a fiber denier of about 3 d and about 40 weight percent single component polyester fibers that have a fiber denier of about 6 d and that have fiber lengths of from about 3.8 to about 5.08 centimeters.

The ventilation layer 32 can be of any desired shape. Suitable shapes include for example, circular, rectangular, triangular, trapezoidal, oblong, dog-boned, hourglass-shaped, or oval. The ventilation layer 32 may extend beyond, completely over or partially over the absorbent body 24. For example, the ventilation layer 32 may suitably be located over the intermediate section 16 of the diaper 10 and be substantially centered side-to-side with respect to the longitudinal centerline 36 of the diaper 10. It is generally desired that the entire absorbent body 24 be overlaid with the ventilation layer 32 to prevent substantially all surface to surface contact between the outer cover 20 and the absorbent body 24. In the illustrated aspects, the ventilation layer 32 is coextensive with the absorbent body 24. This allows for the maximum degree of air exchange with minimal dampness on the garment facing surface of the outer cover 20.

In the illustrated aspects, the ventilation layer 32 is arranged in a direct, contacting liquid communication with the absorbent body 24. The ventilation layer 32 may be operably connected to the outer cover 20 with a conventional pattern of adhesive, such as a swirl adhesive pattern. In addition, the ventilation layer 32 may be operably connected to the absorbent body 24 with a conventional pattern of adhesive. The amount of adhesive add-on should be sufficient to provide the desired levels of bonding, but should be low enough to avoid excessively restricting the movement of air and vapor from the absorbent body 24 and through the outer cover 20.

The preceding detailed description relates to the components of the diaper 10 that are generally known. In order to provide the desired barrier and protective properties, the diapers 10 of the invention may also include skin care compositions.

A skin care composition may be applied to the bodyfacing surface 11 of the bodyside liner 22 of the diaper 10. Ranges may be used to describe the relative amounts of components in the compositions of the invention as well as to describe the relative physical properties of the compositions. These ranges are illustrative and one of skill in the art will recognize that the nature of the composition will dictate the various levels of components that must be used to achieve the intended benefit for the skin barrier. The levels can be determined by routine experimentation in view of the disclosure provided herein. The compositions of the invention can be in a variety of physical forms including emulsions, lotions, creams, ointments, salves, suspensions, encapsulations, gels or hybrids of these forms. The compositions of the invention may be hydrophilic-based or they may be based on primarily non-aqueous components. Both hydrophilic and nonaqueous systems are described herein.

The compositions of the invention that are primarily hydrophilic may include one or more hydrophilic solvents. The hydrophilic solvents provide the "backbone" for the hydrophilic characteristics of the compositions. The hydrophilic solvents give the compositions their overall "hydrophilic" nature and provide the attraction for water and other water-containing molecules. The hydrophilic solvents impart the ability of the entire composition to act as a carrier for bringing lipids into the skin barrier. Hydrophilic solvents include, but are not limited to, water, propylene glycol, low molecular weight polyethylene glycols (molecular weights of less than 720 and liquid at room temperature), methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol solutions, hydrogenated starch hydrolysate, ethoxylated glycerin, silicone glycols and mixtures of such compounds. The compositions of the invention may include from about 10 to about 90 percent by weight of one or more hydrophilic solvents. More specifically, the compositions may include from about 25 to about 75 percent by weight of hydrophilic solvents. Desirably, the compositions of the invention may include from about 30 to about 60 percent by weight of hydrophilic solvents. In particular aspects, the hydrophilic solvent can be at least a minimum of about 10 percent by weight. The hydrophilic solvent can alternatively be at least about 25, and optionally, can be at least about 30 percent by weight of the composition. In other aspects, the hydrophilic solvent can be not more than a maximum of about 90 percent by weight of the composition. The hydrophilic solvent can alternatively be not more than about 75, and optionally, can be not more than about 60 percent by weight of the composition.

The compositions of the invention may also include one or more high molecular weight polyethylene glycols. The high molecular weight polyethylene glycols primarily function to provide the hydrophilic solvents and any active ingredients in solid form at room temperature. The high molecular weight polyethylene glycols also contribute the composition having a penetration hardness of at least 5 mm. In addition to providing a solid medium for the solvent, and reducing its tendency to migrate, the high molecular weight polyethylene glycols provide a tackiness to the hydrophilic lotion composition that improves transfer to the skin of the wearer. As used herein, suitable high molecular weight polyethylene glycols include, but are not limited to, the following materials: polyethylene glycols having an average molecular weight of 720 daltons or greater and mixtures of such glycols. These materials are not liquid at room temperature. Particularly suitable high molecular weight polyethylene glycols can have an average molecular weight of from 720 to about 1,840,000 daltons, more specifically from about 1400 to about 440,000 daltons, and still more specifically from about 1760 to about 10,570 daltons. The compositions of the invention may include from about 5 to about 90 percent by weight of one or more high molecular weight polyethylene glycols. More specifically, the compositions may include from about 10 to about 50 percent by weight of high molecular weight polyethylene glycols. Desirably, the compositions of the invention may include from about 15 to about 25 percent by weight of high molecular weight polyethylene glycols. In particular aspects, the high molecular weight polyethylene glycol can be at least a minimum of about 5 percent by weight. The high molecular weight polyethylene glycol can alternatively be at least about 10, and optionally, can be at least about 15 percent by weight of the composition. In other aspects, the high molecular weight polyethylene glycol can be not more than a maximum of about 90 percent by weight of the composition. The high molecular weight polyethylene glycol can alternatively be not more than about 50, and optionally, can be not more than about 25 percent by weight of the composition.

The compositions of the invention may further include one or more fatty alcohols. The fatty alcohols, combined with the high molecular weight polyethylene glycols, provide the solid form for the compositions at room temperature. The fatty alcohols also contribute to the composition having a penetration hardness of at least 5 mm. The fatty alcohols contribute to the solid nature of the compositions and, thereby, assist in maintaining and stabilizing the compositions on the bodyfacing surface 11 of the bodyside liner 22. Suitable fatty alcohols include, but are not limited to, the following materials: alcohols having a carbon chain length of $C_{14}$-$C_{30}$ or greater, including cetyl alcohol, stearyl alcohol, arachidyl alcohol, behenyl alcohol, and mixtures thereof. The compositions of the invention may also include one or more $C_{14}$-$C_{30}$ fatty acids. Suitable fatty acids include, but are not limited to carboxylic acids having a carbon chain length of $C_{12}$ to $C_{30}$ or greater including palmitic acid, stearic acid and other such acids. The compositions of the invention may include from about 1 to about 40 percent by weight of one or more fatty alcohols. More specifically, the compositions may include from about 10 to about 25 percent by weight of fatty alcohols. Desirably, the compositions of the invention may include from about 15 to about 20 percent by weight of fatty alcohols. In particular aspects, the fatty alcohols/fatty acids can be at least a minimum of about 1 percent by weight. The fatty alcohols/fatty acids can alternatively be at least about 10, and optionally, can be at least about 15 percent by weight of the composition. In other aspects, the fatty alcohols/fatty acids can be not more than a maximum of about 40 percent by weight of the composition. The fatty alcohols/fatty acids can alternatively be not more than about 25, and optionally, can be not more than about 20 percent by weight of the composition.

Additional components may be added to the hydrophilic compositions of the invention in order to provide additional skin health benefits. The hydrophilic compositions of the invention may also include one or more emulsifying surfactants, including oil-in-water emulsifying surfactants. The surfactants provide for the incorporation of lipid (fats, oils, sterols and sterol derivatives, etc.) and other (emollient) components of the composition into the hydrophilic solvent(s). By emulsifying the lipid and other components into the hydrophilic solvent(s), the surfactants contribute to the delivery of the lipids and other beneficial compounds to the skin barrier. Emulsifying surfactants are employed typically in cosmetic preparations to form emulsions of various components. The immiscible phase, such as an oil, is dispersed as droplets in the continuous phase, such as water or in this case the hydrophilic solvent.

Suitable surfactants include, but are not limited to, Emulsifying Wax NF, Glyceryl Stearate SE, Glycol Stearate SE, Glycereth-20 Stearate, Glyceryl Hydroxystearate, Glyceryl Laurate SE, Glyceryl Oleate SE, Propylene Glycol Oleate SE, Propylene Glycol Stearate SE, Sorbitan Stearate, water dispersible metal soaps (Sodium Stearate), Polyoxyethylene 25 Hydrogenated Castor Oil, Polyoxyethylene 75 Sorbitan Lanolin Derivative, Polyoxyethylene 50 Lanolin Derivative, Polyoxyethylene 4 Lauryl Ether, Polyoxyethylene 23 Lauryl Ether, Polyoxyethylene 10 Cetyl Ether, Polyoxyethylene 10 Stearyl Ether, Polyoxyethylene 20 Stearyl Ether, Polyoxyethylene 10 Oleyl Ether, Polyoxyethylene 20 Oleyl Ether, Polysorbate 20, Polysorbate 21, Polysorbate 40, Polysorbate 60, Polysorbate 65, Polysorbate 80, Polysorbate 81, Polysorbate 85, Dimethicone Copolymers and mixtures thereof. The surfactants of the composition may also be characterized as having a combined HLB in a range greater than 7. Therefore, one or more surfactants can be selected for use in the composition and their combined HLB would be in a range greater than 7. The compositions of the invention may include from about 1 to about 20 percent by weight of one or more emulsifying surfactants having a combined HLB in a range greater than 7. More specifically, the compositions may include from about 2 to about 15 percent by weight of surfactants. Desirably, the compositions of the invention may include from about 3 to about 10 percent by weight of surfactants. In particular aspects, the surfactants can be at least a minimum of about 1 percent by weight. The surfactants can alternatively be at least about 2, and optionally, can be at least about 3 percent by weight of the composition. In other aspects, the surfactants can be not more than a maximum of about 20 percent by weight of the composition. The surfactants can alternatively be not more than about 15, and optionally, can be not more than about 10 percent by weight of the composition.

The hydrophilic compositions of the invention may also include fats and oils that provide a source of essential and non-essential fatty acids similar to those found in the skin's natural barrier. Fats and oils include compounds that are fats, oils, essential oils, fatty acids, fatty alcohols, phospholipids and mixtures of such compounds. Fats and oils include oils derived from plant and animal sources. Similarly, the essential oils include essential oils derived from plant sources.

Those of skill in the art would understand that all compounds commonly understood to have the structure of or to function as fats, oils, essential oils, fatty acids, fatty alcohols and phospholipids can be used as the natural fat or oil component of the composition of the invention. While an exhaustive list of each and every fat and oil that could be used in the compositions of the invention is not provided, those of skill in the art will understand and appreciate the individual compounds that may serve as a fat or oil component of the compositions of the invention.

Representative examples of fats and oils include, but are not limited to: Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lanolin, Lanolin Alcohol, Lauric Acid, Palmitic Acid, Stearic Acid, Linoleic Acid, Stearyl Alcohol, Lauryl Alcohol, Myristyl Alcohol, Benenyl Alcohol, Rose Hip Oil, Calendula Oil, Chamomile Oil, Eucalyptus Oil, Juniper Oil, Sandlewood Oil, Tea Tree Oil, Sunflower Oil, and Soybean Oil. Another suitable fat/oil for the compositions of the invention is PROLIPID 141 blend available from International Specialty Products of Wayne, N.J. The PROLIPID 141 blend is a mixture of glyceryl stearate, fatty acids, fatty alcohols and phospholipids.

In order to assist in replenishing skin barrier protecting and enhancing agents, the compositions of the invention may include fats and oils in an amount of from about 0.1 to about 30 percent by weight, desirably from about 0.5 to about 25 percent by weight, and more desirably from about 1 to about 20 percent by weight of the composition. In particular aspects, the fats and oils can be at least a minimum of about 0.1 percent by weight. The fats and oils can alternatively be at least about 0.5, and optionally, can be at least about 1 percent by weight of the composition. In other aspects, the fats and oils can be not more than a maximum of about 30 percent by weight of the composition. The fats and oils can alternatively be not more than about 25, and optionally, can be not more than about 20 percent by weight of the composition.

The hydrophilic compositions of the invention may also include sterols and sterol derivatives that act in combination with the natural fats/oils to provide natural skin barrier enhancement and skin barrier recovery. Sterols and sterol derivatives that can be used in the compositions of the invention include, but are not limited to: β-sterols having a tail on the 17 position and having no polar groups for example, cholesterol, sitosterol, stigmasterol, and ergosterol, as well as, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyidecanoate, dihydrolanosterol, dihydrolanosteryl octyldecanoate, ergocalciferol, tall oil sterol, soy sterol acetate, lanasterol, soy sterol, avocado sterols, "AVOCADIN" (trade name of Croda Ltd. of Parsippany, N.J.), sterol esters, and similar compounds, as well as mixtures thereof. The compositions of the invention may include sterols, sterol derivatives or mixtures of both sterols and sterol derivatives in an amount of from about 0.1 to about 10 percent by weight, desirably from about 0.5 to about 5 percent by weight and more desirably from about 0.8 to about 3 percent by weight of the composition. In particular aspects, the sterols can be at least a minimum of about 0.1 percent by weight. The sterols can alternatively be at least about 0.5, and optionally, can be at least about 0.8 percent by weight of the composition.

In other aspects, the sterols can be not more than a maximum of about 10 percent by weight of the composition. The sterols can alternatively be not more than about 5, and optionally, can be not more than about 3 percent by weight of the composition.

To provide improved stability and transfer to the skin of the wearer, the hydrophilic compositions of the invention may include one or more emollients. The emollients of the compositions act as lubricants to reduce the abrasiveness of the bodyside liner 22 to the skin and, upon transfer to the skin, help to maintain the soft, smooth and pliable appearance of the skin. In general, emollients are skin-conditioning ingredients that help to soften, smooth, plasticize, lubricate, moisturize, improve the appearance of, improve the feel of and protect skin. The hydrophilic compositions of the invention may include from about 0.1 to about 10 percent by weight of one or more emollients. More specifically, the compositions may include from about 0.5 to about 5 percent by weight of emollient(s). Even more specifically, the compositions may include from about 1 to about 5 percent by weight of emollient(s). In particular aspects, the emollients can be at least a minimum of about 0.1 percent by weight. The emollients can alternatively be at least about 0.5, and optionally, can be at least about 1 percent by weight of the composition. In other aspects, the emollients can be not more than a maximum of about 10 percent by weight of the composition. The emollients can alternatively be not more than about 5 percent by weight of the composition.

Suitable emollients include petroleum based oils, petrolatum, vegetable oils, mineral oils, alkyl dimethicones, alkyl methicones, alkyldimethicone copolyols, phenyl silicones, alkyl trimethylsilanes, dimethicone, lanolin and its derivatives, esters, glycerol esters and their derivatives, propylene glycol esters and their derivatives, alkoxylated carboxylic acids, alkoxylated alcohols, fatty alcohols and mixtures of such compounds.

The hydrophilic compositions of the invention may also include the emollient and skin protectant, dimethicone. The dimethicone can be blended with the other components of the composition through the addition of water-based emulsions containing dimethicone such as emulsions having the trade designations "Dow Corning 1669 Emulsion" and "Dow Corning 1664 Emulsion" available from Dow Corning of Midland, Mich. The dimethicone can also be blended using a microencapsulated dimethicone such as are available from Lipo Technologies of Dayton, Ohio or from 3M of St. Paul, Minn. The dimethicone can also be added to the hydrophilic compositions of the invention in the form of an entrapped dimethicone. Dimethicone can be entrapped in "Polytrap" or "Microsponges" as are available from Advanced Polymer Systems of San Francisco, Calif. The dimethicone can also be incorporated in the form of a dimethicone treated powder such as dimethicone-treated talc or dimethicone-treated zinc oxide as are available from KOBO of South Plainfield, N.J.

Optionally, the hydrophilic compositions of the invention may include from about 1 percent by weight to about 20 percent by weight of one or more viscosity enhancers. The viscosity enhancers can be added to increase the melt point viscosity of the compositions. Increasing the melt point viscosity gives better stability of the compositions on the body-facing materials of the articles. The viscosity enhancers also improve the stability of the composition at a "hot box car" stability temperature of about 130° F. (54.5° C.). The viscosity enhancer increases the meltpoint viscosity of the compositions to have a high viscosity (greater than about 50,000 centipoise) under low shear at the "hot box car" stability temperature of about 54.5° C. and at lower temperatures.

Having viscosity at elevated temperatures prevents the compositions from migrating into or away from the materials to which they are applied. However, the viscosity enhancer component also provides a low viscosity (less than about 5,000 centipoise) under shear for the compositions at process conditions. Typically, process temperatures are approximately 5° C. above the melting point of the composition. Generally, the process temperature is about 60° C. or higher. Different compositions of the invention will have different melting points. The viscosity enhancers of the invention are capable of maintaining the viscosity of compositions of the invention up to temperatures just below the desired processing temperature for a given composition.

Suitable viscosity enhancers can include, but are not limited to, Actrylamides Copolymers, Agar, Gelatin, Water-Dispersable Metal Soaps, Butoxy Chitosan, Calcium Carboxymethyl Cellulose, Calcium Alginate, Carbomer, Carboxybutyl Chitosan, Carboxymethyl Chitosan, Carboxymethyl Dextran, Carboxymethyl Hydroxyethyl Cellulose, Cellulose Gum, DMAPA Acrylates/Acrylic Acid/Acrylonitrogens, Hectorite, Hydrated Silica, Hydroxyethyl Cellulose, Hydroxypropyl Guar, Hydroxypropyl Methylcellulose, Isobutylene/Sodium Maleate Copolymer, Kelp, Lithium Magnesium Silicate, Lithium Magnesium Sodium Silicate, Alumina Magnesium Silicate, Smectite, Organomodified Clays, Magnesium/Aluminum/Hydroxide/Carbonate, Magnesium Aluminum Silicate, Magnesium Silicate, Magnesium Trisilicate, Methoxy PEG-22/Dodecyl Glycol Copolymer, Methyl Cellulose, Methyl Hydroxyethylcellulose, Microcrystalline Cellulose, Montmorillonite, Nonoxynol Hydroxyethylcellulose, PEG Crosspolymer, Polyacrylate-3, Polyacrylic Acid, Polyethylene/isopropyl Maleate Copolymer, Polymethacrylic Acid, Polyvinyl Alcohol, PVP/Decene Copolymer, PVP Montmorillonite, Sodium Acrylates Copolymer, Sodium Acrylate/Vinyl Alcohol Copolymer, Sodium Acrylates/Vinyl Isodecanate Crosspolymer, Partially Crosslinked Polyacrylic Acid Polymers, Sodium Carboxymethyl Starch, Sodium Hydroxypropyl Starch Phosphate, Sodium Polyacrylate, TEA Alginate, TEA Carbomer, Xanthan Gum, Locust Bean Gum, Yeast Polysaccharides and mixtures thereof.

The hydrophilic compositions of the invention may also include one or more rheology modifiers or suspending agents to prevent separation of components of the compositions during processing. Various components of the compositions including those that may be in particulate form or those that may be in the form of emulsion droplets are susceptible to "settling out" during the processing of the compositions, particularly if there is an equipment shut down. The rheology modifiers of the invention have been found to increase the viscosity of the compositions at process temperatures and to prevent the settling out of more dense components of the compositions. The rheology modifiers deliver this benefit even under low shear conditions. The hydrophilic compositions of the invention may include from about 0.5 to about 10 percent by weight of a rheology modifier. Suitable rheology modifiers can be selected from natural clays, synthetic analogs of natural clays, alginates, starches, natural gums and mixtures of such compounds. Natural clays include montmorillonite, bentonite, beidellite, hectorite, saponite, stevensite, magnesium aluminum silicate and similar clays. Synthetic analogs of natural clays, such as LAPONITE synthetic clay available from Southern Clay Products, Inc. of Gonzales, Tex. can also be used to provide the rheology benefit to compositions of the invention.

The nonaqueous compositions of the invention may have some components in common with the hydrophilic compositions. The nonaqueous compositions of the invention may include an emollient component-like the hydrophilic compositions—however, the percentage of the total composition may be higher. Suitable emollients that may be incorporated into the nonaqueous compositions of the invention include oils such as petroleum based oils, petrolatum, vegetable based oils, hydrogenated vegetable oils, animal oils, hydrogenated animal oils, mineral oils, natural or synthetic oils, alkyl dimethicones, alkyl methicones, alkyldimethicone copolyols, phenyl silicones, siliconized waxes, alkyl trimethylsilanes, dimethicone, lanolin and its derivatives, esters, branched esters, glycerol esters and derivatives, propylene glycol esters and derivatives, alkoxylated carboxylic acids, alkoxylated alcohols, fatty alcohols, triglycerides, alkyl hydroxystearates and mixtures of such compounds. The esters can be selected from cetyl palmitate, stearyl palmitate, cetyl stearate, isopropyl laurate, isopropyl myristate, isopropyl palmitate, behenyl behenate, stearyl behenate, $C_{12}$-$C_{15}$ alkyl fumarate, $C_{20}$-$C_{40}$ alkyl behenate, dibehenyl fumarate, branched esters and mixtures thereof. Ethers such as eucalyptol, cetearyl glucoside, dimethyl isosorbicide polyglyceryl-3 cetyl ether, polyglyceryl-3 decyltetradecanol, propylene glycol myristyl ether and mixtures thereof can also be used as emollients. The fatty alcohols include octyldodecanol, lauryl, myristyl, cetyl, stearyl and behenyl alcohol, $C_{24}$ and greater fatty alcohols and mixtures thereof. For example, a particularly well suited emollient is petrolatum. Other conventional emollients may also be added in a manner that maintains the desired properties of the compositions set forth herein.

To provide improved stability and transfer to the skin of the wearer, the nonaqueous compositions of the invention may include from about 1 to about 95 percent by weight, desirably from about 20 to about 75 percent by weight, and more desirably from about 40 to about 60 percent by weight of the emollient. In particular aspects, the emollient can be at least a minimum of about 1 percent by weight. The emollient can alternatively be at least about 20 percent, and optionally, can be at least about 40 percent to provide improved performance. In other aspects, the emollient can be not more than a maximum of about 95 percent by weight. The emollient can alternatively be not more than about 75 percent, and optionally, can be not more than about 60 percent to provide improved effectiveness. Compositions that include an amount of emollient greater than the recited amounts tend to have lower viscosities that undesirably lead to migration of the composition. Whereas, compositions that include an amount of emollient less than the recited amounts tend to provide less transfer to the wearer's skin.

The nonaqueous compositions of the invention may also include one or more solidifying agents. The solidifying agents of the present invention primarily function to solidify the composition so that the composition is a solid at room temperature and has a penetration hardness of at least 5 mm and has a melting point of at least 32° C. The solidifying agent may also provide a tackiness to the composition that improves the transfer by adhesion to the skin of the wearer. Depending on the solidifying agent selected, the solidifying agent can also modify the mode of transfer so that the composition tends to fracture or flake off instead of actually rubbing off onto the skin of the wearer which can lead to improved transfer to the skin. The solidifying agent may further function as an emollient, occlusive agent, moisturizer, barrier enhancer, viscosity enhancer and combinations thereof. The solidifying agents may include waxes as well as compounds that perform functionally as waxes.

The solidifying agents may be selected from alkyl siloxanes, polymers, hydrogenated vegetable oils having a melting point of 35° C. or greater, fatty acid esters and branched esters with a melting point of 35° C. or greater, alkyl hydroxystearates ($>C_{16}$), alkoxylated alcohols and alkoxylated carboxylic acid. Additionally, the solidifying agents can be selected from animal, vegetable and mineral waxes, synthetic waxes and alkyl silicones. Examples of solidifying agents include, but are not limited to, the following: alkyl silicones, alkyl trimethylsilanes, beeswax, behenyl behenate, behenyl benzoate, $C_{24}$-$C_{28}$ alkyl dimethicone, $C_{30}$ alkyl dimethicone, cetyl methicone, stearyl methicone, cetyl dimethicone, stearyl dimethicone, cerotyl dimethicone, candelilla wax, carnauba, synthetic carnauba, PEG-12 carnauba, cerasin, hydrogenated microcrystalline wax, jojoba wax, microcrystalline wax, lanolin wax, ozokerite, paraffin, synthetic paraffin, cetyl esters, behenyl behenate, $C_{20}$-$C_{40}$ alkyl behenate, $C_{12}$-$C_{15}$ lactate, cetyl palmitate, stearyl palmitate, isosteryl behenate, lauryl behenate, stearyl benzoate, behenyl isostearate, cetyl myristate, cetyl octanoate, cetyl oleate, cetyl ricinoleate, cetyl stearate, decyl oleate, di-$C_{12}$-$C_{15}$ alkyl fumerate, dibehenyl fumerate, myristyl lactate, myristyl lignocerate, myristyl myristate, myristyl stearate, lauryl stearate, octyldodecyl stearate, octyldodecyl stearoyl stearate, oleyl arachidate, oleyl stearate, tridecyl behenate, tridecyl stearate, tridecyl stearoyl stearate, pentaerythrityl tetrabehenate, pentaerythritylhydrogenated rosinate, pentaerythrityl distearate, pentaerythrityl tetraabeite, pentaerythrityl tetracocoate, pentaerythrityl tetraperlargonate, pentaerythrityl tetrastearate, ethylene vinyl acetate, polyethylene, hydrogenated cottonseed oil, hydrogenated vegetable oil, hydrogenated squalene, hydrogenated coconut oil, hydrogenated jojoba oil, hydrogenated palm oil, hydrogenated palm kernel oil, hydrogenated olive oil, polyamides, metal stearates and other metal soaps, $C_{30}$-$C_{60}$ fatty alcohols, $C_{20+}$ fatty amides, polypropylene, polystyrene, polybutane, polybutylene terephthalate, polydipentane, polypropylene, zinc stearate, dodecyl laurate, stearyl palmitate, octadecyl hexadecanoate, octadecyl palmitate, stearyl behenate, docosyl octanoate, tetradecyl-octadecanyl behenate, hexadecyl-cosanyl hexacosanate, shellac wax, glycol montanate, fluoranated waxes, $C_{20}$-$C_{40}$ alkyl hydroxystearyl stearate and mixtures of such compounds. Suitable branched esters include tetradecyl-octadecanyl behenate and hexadecyl-cosanyl-hexacosanate. In one aspect, the solidifying agent is a blend including about 70 weight percent cerasin wax, about 10 weight percent microcrystalline wax, about 10 weight percent paraffin wax and about 10 weight percent cetyl esters (synthetic spermaceti wax).

Appropriate solidifying agents also include alkylmethylsiloxanes that can be described as non-volatile, occlusive silicone-aliphatic hydrocarbon hybrid waxes. An example of an alkylmethylsiloxane wax is a poly(n-alkylmethylsiloxane) dimethylsiloxane. The poly(n-alkylmethylsiloxane)dimethylsiloxane can have an n-alkyl substitution of an average of 16 carbon atoms or above with an average of more than 2 alkyl groups per molecule, with hydrocarbon contents of at least 40% and with an average molecular weight of at least 1800 or higher. Examples of desirable alkylmethylsiloxanes for use in the compositions of the invention include random copolymers having the following formula:

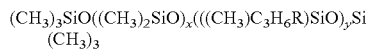

The "R" component of the formula can be an aliphatic hydrocarbon substituent where the chain length is from $C_4$ to $C_{45}$. In particular, "R" can be $C_{16}$, $C_{16-18}$, $C_{20-24}$ or $C_{30-45}$. For example, $C_{30-45}$ alkylmethylsiloxane is commercially available as trade designation "SF1642" from General Electric Silicones or "AMS-$C_{30}$" from Dow Corning Silicones. The value of "x" is on average more than 2 and the value of "y" is at least 1. The nature of the alkylmethylsiloxane must be balanced between its compatibility with dimethicone or polydimethyl siloxane and its compatibility with organic compounds like petrolatum and waxes. For example, as "x" increases, "y" decreases and "R" is small, the molecule increases its compatibility with dimethicone but decreases its compatibility with organic compounds. Alternatively, as "x" decreases, "y" increases and "R" is $C_{18+}$, the molecule decreases its compatibility with dimethicone but increases its compatibility with organic compounds. These solidifying agents can be used to stabilize dimethicone-containing compositions of the invention.

To provide improved transfer to the skin of the wearer, the composition may include from about 5 to about 95 percent by weight, desirably from about 25 to about 75 percent by weight, and more desirably from about 30 to about 50 percent by weight of solidifying agent(s). In particular aspects, the solidifying agent can be at least a minimum of about 5 percent by weight. The solidifying agent can alternatively be at least about 25 percent, and optionally, can be at least about 30 percent to provide improved performance. In other aspects, the solidifying agent can be not more than a maximum of about 95 percent by weight. The solidifying agent can alternatively be not more than about 75 percent, and optionally, can be not more than about 50 percent to provide improved effectiveness. Compositions that include an amount of solidifying agent less than the recited amounts tend to be too soft and may have lower viscosities that may undesirably lead to migration of the composition away from bodyfacing surfaces 11 of the absorbent article, thus diminishing transfer to the wearer's skin. Whereas, compositions that include an amount of solidifying agent greater than the recited amounts tend to provide less transfer to the wearer's skin.

As with the hydrophilic compositions of the invention, one or more viscosity enhancers may be added to the nonaqueous compositions to increase the viscosity, to help stabilize the formulation on the bodyfacing surface 11 of the bodyside liner 22 and, thereby, to reduce migration and improve transfer to the skin. Examples of suitable viscosity enhancers for the nonaqueous compositions include polyolefin resins, lipophilic/oil thickeners, ethylene/vinyl acetate copolymers, organically modified clays, polyethylene, silica, silica silylate, silica methyl silylate, colloidal silicone dioxide, cetyl hydroxy ethyl cellulose, other organically modified celluloses, PVP/decane copolymer, PVM/MA decadiene crosspolymer, PVP/eicosene copolymer, PVP/hexadecane copolymer, microcrystalline wax, hexadecyl-cosanyl-hexacosanate, shellac wax, glycol montanate, PEG-12 carnauba, synthetic paraffin, ozokerite, $C_{20}$-$C_{40}$ alkyl hydroxystearyl stearate, polyperfluoromethylisopropylether montan wax and mixtures of these compounds. A particularly well suited viscosity enhancer is an ethylene/vinyl acetate copolymer commercially available from E. I. Dupont De Ne Mours under the trade designation "ELVAX". Additionally, the compounds identified herein as suitable solidifying agents may also function as viscosity enhancers to benefit the rheology of the nonaqueous compositions of the invention.

To provide the improved transfer to the skin of the wearer, the nonaqueous compositions may include from about 0.1 to about 40 percent by weight, desirably from about 3 to about 20 percent by weight, and more desirably from about 5 to about 10 percent by weight of the viscosity enhancer for reduced migration and improved transfer to the wearer's skin. In particular aspects, the viscosity enhancer can be at least a minimum of about 0.1 percent by weight. The viscosity enhancer can alternatively be at least about 3 percent, and optionally, can be at least about 5 percent to provide improved performance. In other aspects, the viscosity enhancer can be not more than a maximum of about 40 percent by weight. The viscosity enhancer can alternatively be not more than about 20 percent, and optionally, can be not more than about 10 percent to provide improved effectiveness.

The nonaqueous compositions of the invention may also include one or more natural fats or oils. The nonaqueous compositions may include from about 0.1 to about 48% by weight of one or more of the natural fats or oils identified as being suitable for the hydrophilic compositions of the invention. Additionally, the nonaqueous compositions of the invention may also include one or more sterols or sterol derivatives. The nonaqueous compositions may include from about 0.1 to about 10% by weight of one or more of the sterols or sterol derivatives identified as being suitable for the hydrophilic compositions of the invention.

The nonaqeuous compositions of the invention may also include one or more rheology modifiers. The nonaqeuous compositions may include from about 0.5 to about 20 percent by weight of one or more rheology modifiers selected from silica, silica silylate, silica methyl silylate, quaternary starch compounds, quaternary modified clays, organically modified clays and mixtures thereof. Additionally, the nonaqeuous compositions of the invention may include from about 1 to about 20 percent by weight of one or more clays selected from natural clays and synthetic analogs of natural clays.

Both the hydrophilic and the nonaqueous compositions of the invention may include one or more extracted botanical actives. The extracted botanical actives of the compositions are extracts, containing the chemically "active" components, of various plants and plant substances. The extracted botanical actives, in combination with the other components of the composition, provide several benefits to the skin, particularly skin that is frequently covered by an absorbent article and that is exposed to biological insults. Extracted botanical actives can include any water-soluble or oil-soluble active extracted from a particular plant. Examples of suitable extracted botanical actives are actives extracted from echinacea, yucca glauca, willow herb, basil leaves, Cuban basil, sweet basil, aspic, lavender, arkin, avocado GW, cabbage rose, Turkish oregano, carrot root, grapefruit fruit, fennel fruit, rosemary, thyme, blueberry, bell pepper, black tea, blackberry, black currant fruit, cat's claw, cemila oleifera, coffee seed, Chinese tea, dandelion root, date palm fruit, garcinia, glenn of oak, gingko leaf, green tea polyphenols (i.e. including epicatechin gallate and epigallocatechin 3-O-gallate), hawthorn berries, hexaplant richter, hibiscus special, hydrocotyl, licorice, oolong tea, sage, strawberry, sweet pea, tomato, vanilla fruit, neohesperidin, quercetin, rutin, morin, myricetin, chlorogenic acid, glutathione, glycyrrhizin, absinthe, arnica, centella asiatica, chamomile and constituents thereof (i.e., alpha-bisabolol), comfrey, cornflower, grape seed and constituents thereof (i.e., proanthocyanidins), horse chestnut, ivy (*Herdera helix*), magnolia, milk thistle, mimosa, oat extract, pansey, phytexcell arnica, phytoplenolin, St. John's Wort, sage GW, sage special, sedaplant richter, scullcap, seabuckthorn, white nettle, white tea, witch hazel, yarrow and any combinations thereof. Particular benefits have been observed with compositions including echinacea, yucca glauca, willow herb, grape seed and constituents thereof (i.e., proanthocyanidins), green tea, white tea, black tea, oolong tea, Chinese tea, tea components and mixtures of such compounds. Echinacea actives may be obtained from the following echinacea species: *Echinacea angustifolia, Echinacea purpurea* and *Echinacea pallida*. Varieties of black tea include Flowery Orange Pekoe, Golden Flowery Orange Pekoe and Fine Tippy Golden Flowery Orange Pekoe. Varieties of green tea include Japanese, Green Darjeeling, apple green tea, black currant green tea, cranberry green tea, grapefruit green tea and orange green tea.

Both the hydrophilic and the nonaqueous compositions of the invention may include from about 0.1 to about 15 percent by weight of one or more extracted botanical actives. More specifically, the compositions may include from about 0.5 to about 8 percent by weight of one or more extracted botanical actives. Even more specifically, the compositions include from about 1 to about 5 percent by weight of extracted botanical actives. In particular aspects, the extracted botanical actives can be at least a minimum of about 0.1 percent by weight. The extracted botanical actives can alternatively be at least about 0.5, and optionally, can be at least about 1 percent by weight of the composition. In other aspects, the extracted botanical actives can be not more than a maximum of about 15 percent by weight of the composition. The extracted botanical actives can alternatively be not more than about 8, and optionally, can be not more than about 5 percent by weight of the composition. Botanicals are primarily extracts of the plants from which they originate and botanicals are available from suppliers as part of a composition that also contains an extracting solvent. Amounts of the botanicals in the compositions of the invention in terms of active component (not extract) may range from about 0.000001 to about 15% by weight. Desirably, the amount of active botanical is from about 0.00001 to about 5% and more desirably from about 0.0001 to about 1% by weight of the composition. Further, it is also desirable that the amount of active botanical is from about 0.0001 to about 0.5% of the composition and more desirably from about 0.001 to about 0.1% by weight of the composition.

The extracted botanical actives are available from numerous suppliers. For example, Echinacea extract is available from Bio-Botanica of Hauppauge, N.Y. Yucca Glauca extract is available from Brooks of South Plainfield, N.J. Canadian Willow Herb is available from Fytokem of products of Saskatchewan, Canada. Borage seed oil is available from Loders Croklaan of England. Green tea concentrate or extract (solid), green tea extract (liquid), grape seed extract (solid) and white tea 50% (solid) are available from Symrise, formerly DRAGOCO (Totowa, N.J.). The actual percentages of active botanicals in the extract composition are typically proprietary to the supplier of the extract.

If it is desired that the compositions of the invention provide a treatment for the skin, the compositions of the invention, both hydrophilic and nonaqueous, can also include an active ingredient such as a diaper rash skin protectant. Skin protectants are drug products that protect injured or exposed skin or mucous membrane surface from harmful or annoying stimuli. Suitable active ingredients, in addition to those mentioned above as suitable emollients, that can be incorporated into the composition include, but are not limited to, allantoin and its derivatives, aloe, aluminum hydroxide gel, calamine, cocoa butter, dimethicone, cod liver oil, kaolin and its derivatives, lanolin and its derivatives, mineral oil, petrolatum, shark liver oil, talc, topical starch, zinc acetate, zinc carbonate, zinc oxide and mixtures thereof. The compositions may include from about 0.10 to about 85 percent by weight of the active ingredient depending upon the skin protectant, the amount desired to be transferred to the skin and the amount required in a particular FDA skin protectant monograph.

In order to better enhance the benefits to the wearer, additional ingredients can be included in the hydrophilic and nonaqueous compositions of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); antioxidants-cosmetic (reduce oxidation); astringents-cosmetic (induce a tightening or tingling sensation on skin); astringent-drug (a drug product that checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, or that has a topical counterirritant effect by stimulating cutaneous sensory receptors); film formers (to hold active ingredients on the skin by producing a continuous film on skin upon drying); fragrances (consumer appeal); silicones/organomodified silicones (protection, water resistance, lubricity, softness); oils (mineral, vegetable, and animal); Natural Moisturizing Factor (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

An important property of the compositions of the different aspects of the present invention is their ability to remain on the surface of the bodyside liner 22 and their resistance to migration into the diaper 10 such that they can readily be transferred to the wearer's skin. In this regard, the articles having the compositions of the present invention applied to their bodyside liner 22 define a z-direction migration loss of no more than about 55%, desirably no more than about 50%, more desirably no more than about 45%, even more desirably no more than about 40% and yet even more desirably no more than about 35% when subjected to the Z-Direction Lotion Migration Test set forth in PCT Publication WO 02/051456 published on Jul. 4, 2002 and incorporated herein by reference. In articles that have a greater z-direction migration loss, the composition undesirably migrates into the interior and along the surface of the bodyside liner 22 and at times through the bodyside liner 22 into the absorbent body 24 of the article which results in a lower reduction in abrasion and less transfer to the skin of the wearer.

Another important measure of the compositions of the different aspects of the present invention is their ability to resist migration laterally along the surface of the bodyside liner 22. In this regard, the articles having the compositions of the present invention applied to the bodyside liner 22 define a cd-direction migration loss of no more than about 40%, desirably no more than about 35%, more desirably no more than about 30%, even more desirably no more than about 25% and yet even more desirably no more than about 20% when subjected to the CD-Direction Lotion Migration Test set forth in PCT Publication WO 02/051456 published on Jul. 4, 2002. In articles which have a greater cd-direction migration loss, the composition undesirably migrates along the surface of the bodyside liner 22 and at times through the bodyside liner 22 into the absorbent body 24 of the article which results in a lower reduction in abrasion and less transfer to the skin of the wearer.

Moreover, to provide the improved stability and transfer to the skin of the wearer, the compositions of the present invention may define a melting point of from about 32° C. to about 100° C., desirably from about 35° C. to about 80° C., and more desirably from about 40° C. to about 75° C. Compositions that have lower melting points exhibit migration of the composition during use and at elevated temperatures in storage that can undesirably result in reduced transfer to the skin. Whereas, compositions that have higher melting points may require that the composition be at a temperature above the flash point of the bodyside liner 22 material which can undesirably lead to fires. The melting points of the compositions of the invention cause the compositions to be relatively immobile and localized on the bodyfacing surface 11 of the diaper 10 at room temperature and readily transferable to the skin of the wearer at body temperatures. However, the compositions of the invention are not completely liquid under extreme storage conditions. Stability in a solid state at elevated temperatures is made possible, in part, by the melting point and the rheology provided by the high molecular weight polyethylene glycol and the addition of viscosity enhancers and rheology modifiers, if needed, in the composition. Desirably, the compositions are easily transferable to the skin by way of normal contact, wearer motion, adhesion or body heat. When the compositions are relatively immobilized at room temperature, a lesser quantity of composition is required on the bodyfacing surface 11 to provide a beneficial effect.

The composition of the present invention may further define a low shear viscosity of from about 50,000 to about 1,000,000 centipoise, desirably from about 100,000 to about 800,000 centipoise, and more desirably from about 300,000 to about 500,000 centipoise for reduced migration and improved transfer to the skin of the wearer. Compositions that have lower melt point viscosities exhibit migration of the composition through the bodyside liner 22 into the absorbent body 24 of the article which can undesirably result in reduced transfer to the skin. Whereas, compositions that have higher melt point viscosities may be so solid as to also exhibit a reduced transfer to the skin.

Further, to provide the improved stability and transfer to the skin of the wearer, the compositions of the present invention may also define a high shear viscosity of less than about 5,000 centipoise, desirably from about 100 to about 500 centipoise, and more desirably from about 150 to about 250 centipoise at a temperature of about 60° C. (or higher temperatures depending on the components and melting point of the composition).

The penetration hardness of the compositions of this invention can be from about 5 to about 365 millimeters, more desirably from about 10 to about 300 millimeters, more desirably from about 20 to about 200 millimeters, and still more desirably from about 40 to about 120 millimeters. (Compositions having a needle penetration hardness greater than 365 millimeters cannot be measured using ASTM method D 1321). The hardness of the compositions of this invention is important for two reasons. First, the softer the formulation the more mobile the formulation will be, making the formulation more likely to migrate to the inner plies of the diaper 10, which is not desirable. Secondly, softer compositions tend to be more greasy/oily to the touch, which is also less desirable.

Figure 3:
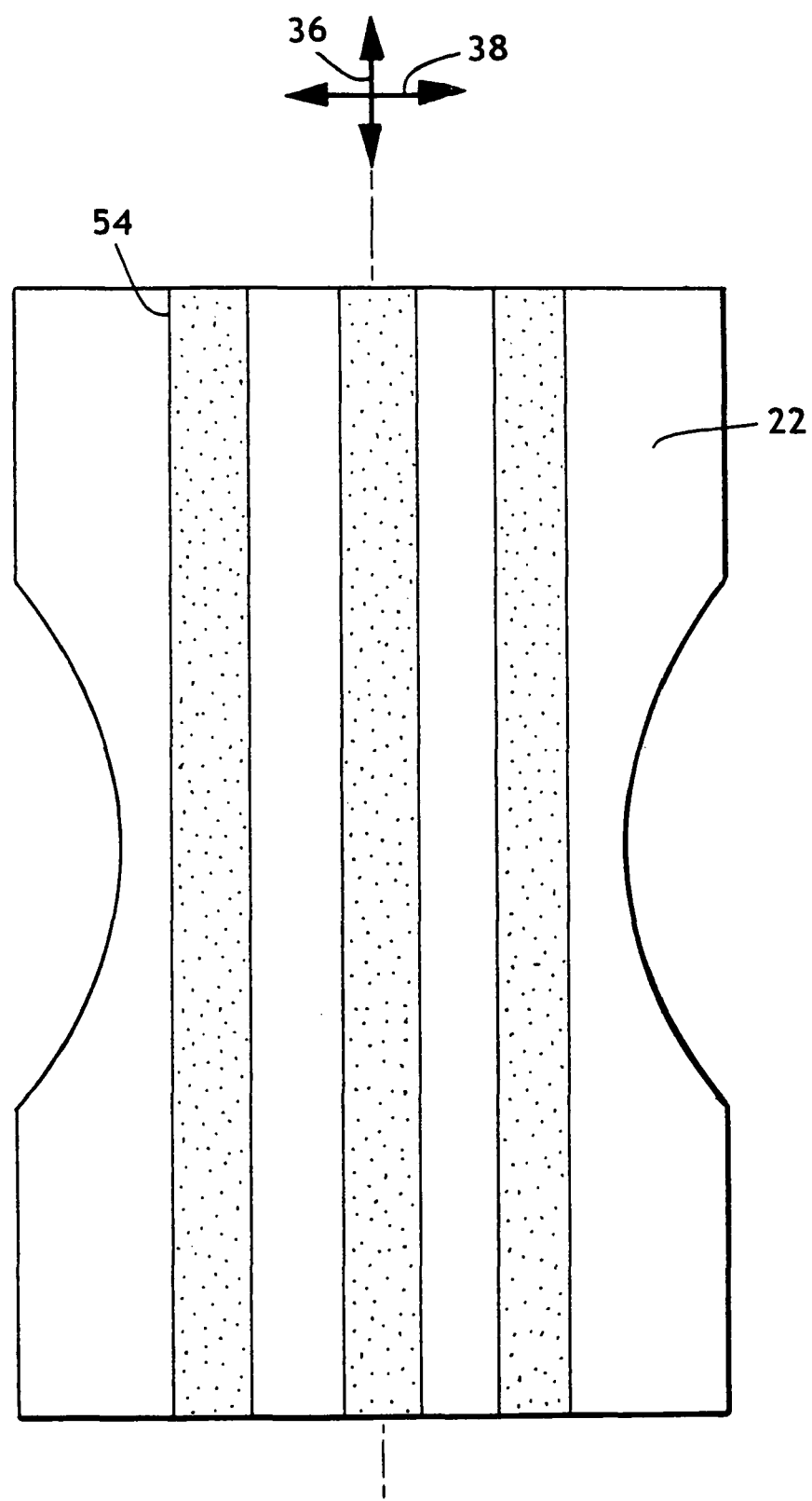
FIG. 3 representatively shows a top plan view of the bodyside liner of the absorbent article of FIG. 1 with the surface that contacts the wearer facing the viewer.

The composition may be applied to the entire bodyfacing surface 11 of the bodyside liner 22 or may be selectively applied to particular sections of the bodyfacing surface 11, such as the medial section along the longitudinal centerline of the diaper 10, to provide greater lubricity of such sections and to transfer such composition to the wearer's skin. Alternatively, the bodyfacing surface 11 of the bodyside liner 22 may include multiple stripes of the composition applied thereto as illustrated in FIG. 3. For example, the bodyfacing surface 11 of the bodyside liner 22 may include from 1 to 20 stripes 54 of composition extending along the longitudinal direction of the diaper 10. The stripes 54 may extend the full length of the bodyside liner 22 or only a portion thereof. The stripes 54 may also define a width of from about 0.2 to about 1 centimeters.

The composition should cover a sufficient amount of the bodyfacing surface 11 of the bodyside liner 22 to ensure adequate transfer to the skin and reduced abrasion between the bodyside liner 22 and the wearer's skin. Desirably, the composition is applied to at least about 5 percent and more desirably at least about 25 percent of the bodyfacing surface 11 of the bodyside liner 22.

The composition can be applied to the bodyside liner 22 at any add-on level that provides the desired transfer benefit. For example, the total add-on level of the composition can be from about 0.05 to about 100 mg/cm$^2$, desirably from about 1 to about 50 mg/cm$^2$ and more desirably from about 10 to about 40 mg/cm$^2$ for improved performance. The add-on amount will depend upon the desired effect of the composition on the skin barrier function and the specific composition. As discussed above, the improved stability and reduced tendency to migrate of the compositions of the present invention allows a lesser amount of composition to be applied to the bodyside liner 22 to achieve the same benefit when compared with conventional compositions.

The composition may be applied to the bodyside liner 22 in any of many well known manners. A preferred method to uniformly apply the composition to the bodyfacing surface 11 of the bodyside liner 22 is spraying or slot coating. Spraying or slot coating the composition is an exact process and offers maximum control of the composition distribution and transfer rate. However, other methods, such as roto-gravure or flexographic printing and foam application can be used. The compositions of the present invention can be applied after the bodyfacing material has been incorporated into the absorbent article or prior to incorporating the body facing material into the absorbent article.

In a series of experiments, the ability of extracted botanical actives (that are components of the compositions of the invention) to inhibit enzyme activity was evaluated. The activity of various enzymes is associated with biological insults and when such enzymes are brought into contact with the skin, either because of a biological insult or otherwise, they are believed to have a detrimental effect on the integrity of the skin. Therefore, if components of the compositions of the invention have an inhibitory effect on such damaging enzymes, the compositions provide a benefit to the skin barrier and to skin health in general. Feces are known to contain enzymes including proteases such as trypsin and chymotrypsin (See Haverback, B. J., Dyce, B. J., Gutentag, P. J., and Montgomery, D. W., "Measurement of Trypsin and Chymotrypsin in Stool", *Gastroenterology.* 44:588-597 (1963); and Barbero, G. J., Sibinga, M. S., Marino, J. M., and Seibel, R., "Stool Trypsin and Chymotrypsin", *Amer. J. Dis. Child,* 112: 536-540 (1966)). In order to illustrate their enzyme inhibition activity, botanical extracts, whether in solid (powder) or liquid form, were tested in solution for their ability to inhibit serine protease (trypsin) activity. The details of the methodology used (identified as the "BAPNA-Trypsin Inhibition Test") are as follows.

Botanical extract testing solutions were prepared to a concentration of 0.1% (w/v) if the botanical extract was a solid or 10% (v/v) if the botanical extract was a liquid. For example, the solutions were prepared by introducing 10 milligrams of solid botanical extract into 10 milliliters of Phosphate Buffered Saline ("PBS"), pH 7.4 (available from Life Technologies of Rockville, Md.) or by introducing 100 microliters of liquid botanical extract into 900 microliters of PBS. Solutions having a percentage of botanical extract less than 0.1% (w/v) or 10% (v/v) can be used if the botanical extract is not soluble at 0.1% (w/v) or 10% (v/v). Serial dilutions of the starting 10% botanical extract solution can be prepared using the PBS as the diluent. For example, up to 11 serial dilutions of the starting 10% (v/v) solution can be made to prepare 12 different concentrations of botanical extract for testing: (1) 10%, (2) 5%, (3) 2.5%, (4) 1.25%, (5) 0.625%, (6) 0.3125%, (7) 0.15625%, (8) 0.078%, (9) 0.039%, (10) 0.0195%, (11) 0.0098%, and (12) 0.0049%. In the case of solutions of botanical extracts prepared from a solid, up to 11 serial dilutions of the starting 0.1% solution can be made to prepare 12 different concentrations of botanical extract for testing: (1) 0.1%, (2) 0.05%, (3) 0.025%, (4) 0.0125%, (5) 0.00625%, (6) 0.003125%, (7) 0.0015625%, (8) 0.00078%, (9) 0.00039%, (10) 0.000195%, (11) 0.000098%, and (12) 0.000049%.

Next, 150 microliters of 100 mM Tris buffer were added to the empty wells of a clear well plate, such as a NUNC IMMUNO clear 96-well plate (VWR Scientific Products, Chicago, Ill.). The pH of the 100 mM Tris buffer solution had been adjusted to about 8.0 utilizing HCl (hydrochloric acid). The Tris buffer is commonly known to those skilled in the art and can be prepared using Tris powder or Tris liquid. At least two wells should be maintained as "control" wells. To the remaining wells (i.e. the "test" wells), 25 microliters of the botanical extract solution was added. Twenty-five microliters of PBS solution was added to the "control" wells in place of the botanical extract solution. For instance, to test each of the dilutions, wells 1 and 2 could have 25 microliters of the 10% botanical extract solution added to them in order to analyze the 10% botanical extract solution in duplicate. Wells 3 and 4 could have 25 microliters of the 5% botanical extract solution added to them in order to analyze the 5% botanical extract solution in duplicate, etc.

A stock solution of the porcine pancreatic trypsin was then prepared by adding the protease (15,200 units/milligram, available from Sigma Chemical Company, St. Louis, Mo.) into 100 millimolar Tris buffer solution (pH adjusted to 8.0 with HCl) to yield a concentration of 4 micrograms of trypsin/milliliter. Twenty-five microliters of the stock trypsin solution was then added to each of the wells. The plates were then incubated at room temperature for 15 minutes. After incubation, 50 microliters of a 5 millimolar solution of N-benzyl-arginine-p-nitroaniline ("BAPNA" solution, available from Sigma Chemical Company, St. Louis, Mo.) was added to each of the wells. The BAPNA solution may be prepared as a stock solution by preparing a 50 millimolar solution of BAPNA in dimethylsulfoxide and diluting the solution to a 5 millimolar working solution with deionized water. Those of skill in the art will recognize that the final concentration of botanical extract in the "test" wells was ¹⁄₁₀ of the concentration of the botanical extract solution as they were originally prepared. For example, the originally prepared 10% (v/v) botanical extract solution became a 1% (v/v) botanical extract solution in the "test" well.

After the BAPNA solution was added, the plate was inserted into a SPECTRAmax PLUS 384 Microplate Reader (available from Molecular Devices, Sunnyvale, Calif.) and optical density measurements (at 405 nanometers) were taken every 20 seconds for a period of 5 minutes to monitor the color change of the solutions. When the trypsin enzyme cleaves the BAPNA substrate, releasing the product p-nitroaniline, a color change occurs. The amount of color change occurring at 405 nanometers per minute corresponds to the amount of p-nitroaniline product produced per minute. Reaction rates (indicated by optical density at 405 nanometers per minute) were determined with each concentration of botanical extract tested and the PBS control (no botanical extract). At least two "test" wells were measured for each concentration of botanical extract solution. The reaction rates from each of the "control" and botanical extract tested wells were averaged. The data were used to determine an "$IC_{50}$" value for each botanical extract by plotting trypsin activity (y-axis) versus botanical extract concentration (percent w/v or v/v)(x-axis). "$IC_{50}$" is defined as the concentration of the botanical extract that inhibits 50% of the trypsin activity.

Table 1. sets forth the $IC_{50}$ results for various botanical extracts evaluated in the manner described above.

TABLE 1

| Botanical | Supplying Company | Company Location | Lot Number/ Catalog Number | BAPNA-Trypsin Inhibition $IC_{50} \times 10^{-3}$ (% v/v or w/v) |
|---|---|---|---|---|
| Aloe Gel | Tn-K Industries | Northvale, NJ | 970217/NA | 1000 (no effect) |
| Apple Extract | Gattefosse | Cedex, France | 23152 | 1000 (no effect) |
| Apple Green Tea | Dragoco | Totowa, NJ | 2/037050/L742477 | 11.5 |
| Arkin Special | Dragoco | Totowa, NJ | 2/032581/L647147 | 44.5 |
| Arnica Special | Dragoco | Totowa, NJ | 2/034591/L641060 | 39.0 |
| Avocado | Dragoco | Totowa, NJ | 2/034599/L645246 | 495.0 |
| Avocado GW | Dragoco | Totowa, NJ | 2/031170/L603922 | 19.0 |
| Black Currant B | Dragoco | Totowa, NJ | 2/036100/P331166 | 1000 (no effect) |
| Black Currant Green Tea | Dragoco | Totowa, NJ | 2/037100/P331166 | 12.5 |
| Cornflower | Gattefosse | Cedex, France | 23593/5009 | 1000 (no effect) |
| Cabbage Rose | Gattefosse | Cedex, France | 22223 | 14.5 |
| *Calendula* MCF 774 Hydro | Gattefosse | Cedex, France | 24243/5015 | 1000 (no effect) |
| Cat's Claw | Bio-botanica | Hauppauge, NY | 951341/9945A | 16.5 |
| Cemila Oleifera | Gattefosse | Cedex, France | 22423 | 4.5 |
| *Centella* | Bio-botanica | Hauppauge, NY | 981177/9869A | 176.0 |
| Chamomile | Bio-botanica | Hauppauge, NY | 980572/9831 | 1000 (no effect) |
| Chamomile Special | Dragoco | Totowa, NJ | 2/033021/694633 | 1000 (no effect) |
| *Chlorella* | Bio-botanica | Hauppauge, NY | 951289/9835 | 1000 (no effect) |
| Concombre GR 316 | Gattefosse | Cedex, France | 19190 | 1000 (no effect) |
| Cranberry B | Dragoco | Totowa, NJ | 2/036600/P15193 | 1000 (no effect) |
| Cranberry Green Tea | Dragoco | Totowa, NJ | 2/037600/4100723 | 6.5 |
| Dandelion | Active organics Glenn Corp. | Lewisville, TX | S72041A/316310-11 | 88.5 |
| Dong Quai | Active organics Glenn Corp. | Lewisville, TX | S64418B/316320-11 | 1000 (no effect) |
| Drago-Oat-Active | Dragoco | Totowa, NJ | 2/060900/25493 | 1000 (no effect) |
| *Garcinia* | Bio-botanica | Hauppauge, NY | 951283/9861 | 400.0 |
| Ginseng GR 471 Hydro | Gattefosse | Cedex, France | 23268/5030 | 1000 (no effect) |
| Glenn of Oak | Glenn Corp. | St. Paul, MN | | 715.0 |
| Glenn of Orange | Glenn Corp. | St. Paul, MN | | 1000 (no effect) |
| Gotu Kola PG 5:1 | Bio-botanica | Hauppauge, NY | | 1000 (no effect) |
| Grape Extract | Gattefosse | Cedex, France | 22151 | 1000 (no effect) |
| Grape Seed | Active organics Glenn Corp. | Lewisville, TX | S76920B/318560-11 | 39.0 |
| Grape Seed Extract (solid) | Dragoco | Totowa, NJ | 2/03199/P17400 | 0.05 |
| Grapefruit | Gattefosse | Cedex, France | 23439 | 1000 (no effect) |
| Grapefruit Green Tea | Dragoco | Totowa, NJ | 2/037150/L4100211 | 12.5 |
| Green Tea | Bio-botanica | Hauppauge, NY | 9945 | 6.0 |

TABLE 1-continued

| Botanical | Supplying Company | Company Location | Lot Number/ Catalog Number | BAPNA-Trypsin Inhibition $IC_{50} \times 10^{-3}$ (% v/v or w/v) |
|---|---|---|---|---|
| Green Tea Conc. | Active organics Glenn Corp. | Lewisville, TX | 308463/300230-94 | 140.0 |
| Green Tea Extra (solid) | Dragoco | Totowa, NJ | 2/031598/3066 | 0.15 |
| Green Tea HS | Alban Muller Intl | Northvale, NJ | 7114309/ | 15.6 |
| Hexaplant Richter | Chemisches Lab. | Berlin, Germany | 732431/243 | 29.5 |
| Hibiscus Special | Dragoco | Totowa, NJ | 2/033115/L651028 | 91.5 |
| Hydrocotyl | Gattefosse | Cedex, France | 22842/5038 | 59.0 |
| Hydrolite-5 | Dragoco | Totowa, NJ | 2/016020/27033 | 1000 (no effect) |
| Kiwi | Gattefosse | Cedex, France | 23311 | 1000 (no effect) |
| White Nettle | Gattefosse | Cedex, France | 22571/5040 | 1000 (no effect) |
| Lavender | Gattefosse | Cedex, France | 21189 | 20.0 |
| Lemon Extract | Gattefosse | Cedex, France | 24126 | 1000 (no effect) |
| Lily | Gattefosse | Cedex, France | 23410/5044 | 1000 (no effect) |
| Horse Chestnut | Gattefosse | Cedex, France | 22043/5046 | 36.0 |
| Horse Chestnut | Indena-Intl. Sourcing | Uppersaddle River, NJ. | EG042 | 12.5 |
| German Chamomile | Indena-Intl. Sourcing | Uppersaddle River, NJ | EG004 | 1000 (no effect) |
| *Matricaria* | Gattefosse | Cedex, France | 21747 | 1000 (no effect) |
| Sweet Clover | Gattefosse | Cedex, France | 23316/5051 | 1000 (no effect) |
| Milk Thistle | Active organics Glenn Corp | Lewisville, TX | S76894A/344000-11 | 215.0 |
| Nab Willow Bark Extract | Brooks Industries | S. Plainfield, NJ | 28392 | 1000 (no effect) |
| Orange Green Tea | Dragoco | Totowa, NJ | 2/037400/P327911 | 9.5 |
| *Phytexcell Arnica* | Croda | Parsippany, NJ | 972/34656 | 245.0 |
| *Phytexcell Mulberry* | Croda | Parsippany, NJ | 1004/34684 | 1000 (no effect) |
| Phytoplenolin | Bio-botanica | Hauppauge, NY | 980510/9870 | 760.0 |
| Purple Coneflower | Bio-botanica | Hauppauge, NY | 951338/9852 | 21.0 |
| Raspberry | Gattefosse | Cedex, France | 23204 | 1000 (no effect) |
| Sage CL | Dragoco | Totowa, NJ | 2/033294/L640225 | 1000 (no effect) |
| Sage GW | Dragoco | Totowa, NJ | 2/031770/L619604 | 20.0 |
| Sage Special | Dragoco | Totowa, NJ | 2/033291/P312506 | 22.0 |
| Sedaplant Richter | Chemisches Lab. | Berlin, Germany | 732384/460 | 20.0 |
| St. John's Wort W/S | Dragoco | Totowa, NJ | 2/032985/L658926 | 27.0 |
| White Mistle Toe | Dragoco | Totowa, NJ | 2/033141/L653324 | 1000 (no effect) |
| White Tea 50% (solid) | Dragoco | Totowa, NJ | 10521/C-14235 | 0.10 |
| Witchhazel GW | Dragoco | Totowa, NJ | 2/031340/L651033 | 99.0 |
| Yarrow | Bio-botanica | Hauppauge, NY | 951336/9958 | 80.0 |

As the data in Table 1 indicates, $IC_{50}$ values determined for the botanical extracts tested ranged from 0.05 to 1000 (no inhibition detected). This would indicate that a botanical extract with an $IC_{50}$ value of 0.05 (e.g. Grape Seed Extract) would be highly effective in neutralizing fecal proteases with trypsin-like activity, in particular those proteases known as serine proteases, whereas a botanical extract with a value of 1000 would have little to no effect.

The ability of extracted botanical actives to reduce the skin irritation response due to fecal enzymes or a fecal extract insult was measured in a series of experiments. To identify a readily-available, and representative enzyme system to be used for measuring irritation response, the enzyme activity of infant feces was measured. Fecal extracts were prepared from infant stool samples by vigorously vortexing the stool in deionized water followed but centrifugation at 4,000 times the force of gravity for 10 minutes. The fluid portion was then filtered through a 0.22 micron cellulose acetate filter; aliquots were prepared and stored at −80° C. The infant fecal extracts were assayed for total protease activity as measured by the ability of the sample to hydrolyze a fluorescent dye-labeled casein substrate (the EnzChek Protease Assay Kit (E-6639) is available from Molecular Probes, Eugene, Oreg.) and by protein content as measured by the DC protein assay kit (available from Bio-Rad, Hercules, Calif.).

Earlier studies had shown that fecal extracts (n=19) prepared with slight modifications to the procedure described herein ranged in trypsin activity from 0.4-402 micrograms/milliliter as measured by the ability of the sample to hydrolyze a fluorescently-labeled trypsin peptide substrate (Boc-Gln-Ala-Arg-AMC HCl, available from BACHEM Calif., Incorporated, Torrance, Calif.). Irritation induced in a skin model (EPIDERM skin culture, available from MatTek Corp., Ashland, Mass.) correlated with the total protease activity per microgram of protein as well as trypsin content of these fecal extracts. Based on literature sources and the measured enzyme activities, a porcine trypsin-chymotrypsin insult (available from Specialty Enzymes of Chino, Calif.) was chosen as the "fecal protease insult", for specified examples that follow. In addition, three infant fecal extracts prepared as described above were pooled and used as the "fecal extract insult" to evaluate botanical extracts for their ability to mitigate a skin "irritation response." Total protease activity per amount of protein of the fecal extract insult as measured using the EnzChek Protease Assay Kit (E-6639) and the DC Protein assay was determined to be 330 Relative Fluorescent Units per microgram total protein determined at 60 minutes with one microliter of extract.

EPIDERM skin cultures (EPIDERM EPI-200, MatTek Corp., Ashland, Mass.), which are cornified, air-interfaced human skin cultures with multiple layers of progressively differentiated keratinocytes that resemble human epidermis, were utilized as an in vitro skin irritation model to evaluate the efficacy of the compositions of the invention. EPIDERM EPI-200 skin cultures can be purchased from MatTek Corporation of Ashland, Mass. Experiments using EPIDERM skin cultures were conducted in six well plates. Typically, an EPIDERM skin culture insert was added to each of the six wells. Each well contained one milliliter of EPIDERM skin culture medium (EPI-100-ASY/Assay Medium, MatTek Corp., Ashland, Ma). The plates were then incubated in a 37° C., 5% $CO_2$ incubator for 30-45 minutes. After the incubation, the surface of the EPIDERM skin culture was examined for any medium. If any was found, the medium was carefully removed using a RAININ PIPETMAN pipette. Fifteen microliters of water, a botanical extract test composition dissolved in water at 0.8% (w/v), a petrolatum test composition as described in Table 3, or petrolatum base control was applied to the surface of the EPIDERM skin culture. In the case of the petrolatum samples, it was necessary to use a positive-displacement pipettor and spread the ointment over the skin culture surface using a glass rod. The cultures with the test compositions/controls applied were incubated in a 37° C., 5% $CO_2$ incubator for 30-60 minutes after which the medium underlying the skin culture was removed and replaced with 1 millilter of fresh, pre-warmed medium. Next, either a 25 microliter aliquot of the "fecal extract insult" or a 10 microliter aliquot of the "fecal protease insult" solution was applied to the surface of the EPIDERM skin culture.

The "fecal protease insult" solution was prepared by diluting a 10 milligrams/milliliter stock solution in 50 mM Sodium Acetate, pH 5.5 and 0.15 M NaCl stored at −80° C. to a working concentration of 500 micrograms/milliliter (examples with petrolatum test compositions) or 250 micrograms/milliliter (examples with botanical extract test compositions, 0.8%, w/v) in PBS, pH 7.4. One milligram of the stock fecal protease insult contains 2558 USP units of trypsin and 298 USP units of chymotrypsin and is available from Specialty Enzymes, Inc. of Chino, Calif.

After application of the "fecal protease insult" or "fecal extract insult" solution to the surface of the EPIDERM skin cultures, the cultures were incubated for up to 24 hours in the 37° C., 5% $CO_2$ incubator.

In one set of examples with the petrolatum test compositions and petrolatum base control, the cultures were removed from the incubator after 6 hours; the underlying medium was removed and stored at −80° C. Test compositions included various green tea (anhydrous and water-in-oil emulsions) and grape seed formulations that are representative of the invention as described in Table 3. The irritation response of the EPIDERM skin culture to the test compositions/control and the fecal protease insult solution was determined by measuring the amount of interleukin-1 alpha (IL-1α) secreted into the underlying medium. Interleukin-1 alpha can be quantified using an Interleukin-1 alpha Quantikine Kit available from R&D Systems of Minneapolis, Minn. Interleukin-1 alpha measurements were converted to $Log_{10}$ for each of the treatments and the averages for each treatment were calculated. In order to determine the ability of the petrolatum test compositions to reduce skin irritation caused by the fecal protease insult, the percent mean reduction of IL-1α was calculated as follows:

$$\% \text{ mean reduction of } IL - 1\alpha = 100 \times \frac{((PJ \text{ control} + \text{insult})\text{result} - (\text{test composition} + \text{insult})\text{result})}{((PJ \text{ control} + \text{insult})\text{result} - (PJ \text{ control} + PBS)\text{result})}$$

(Test composition+insult)result=the measured amount of IL-1α from treatment with a petrolatum test formulation+insult.

(PJ control+insult)result=the measured amount of IL-1α from a treatment with a control petrolatum formulation+insult.

(PJ control+PBS)result=the measured amount of IL-1α from a treatment with a control petrolatum formulation with PBS.

The greater the percent mean reduction of IL-1α, the more effective a petrolatum test composition was at reducing irritation caused by the fecal protease insult. The effect of these petrolatum test compositions at reducing skin irritation in the EPIDERM skin model induced by the fecal protease insult is shown in Table 2.

TABLE 2

| Composition | Botanical Component of Petrolatum Compositions | Mean Reduction of Interleukin-1 Alpha (percentage) |
| --- | --- | --- |
| A | Green tea | 86*; 80* |
| B | Green tea | 61*; 98* |
| C | Green tea | 72*; >100* |
| D | Green tea | 30; 80* |
| E | Grape seed | 58* |
| F | Grape seed | 93*; >100* |
| G | Grape seed | 82*; 50* |

*indicates the composition had a significant mean difference from the fecal protease insult applying a Student's t-test with p < 0.05.

For each of the compositions in Table 2, mean reduction of the inflammatory marker (IL-1α) is shown. Each value is obtained from a single experiment. For each experiment, six replicates for each composition were evaluated. The percent mean IL-1α reduction results in Table 2. demonstrate that various petrolatum formulations containing green tea and grape seed of the invention provide a skin protective effect as evidenced by a reduced irritation response. Both petrolatum formulations containing grape seed and green tea at 5% (weight %) significantly reduced skin irritation induced by fecal proteases.

The formulations for Compositions A-G in Table 2. are described in Table 3. below.

TABLE 3

| Component | A (Wt. %) | B (Wt. %) | C (Wt. %) | D (Wt. %) | E (Wt. %) | F (Wt. %) | G (Wt. %) |
|---|---|---|---|---|---|---|---|
| Penreco Petrolatum USP | 68.0 | 83.0 | 77.0 | 78.0 | 81.9 | 78.0 | 73.1 |
| Gilugel EUG | | | | 5.0 | 5.0 | 5.0 | 5.0 |
| Cabot Cab-o-Sil TS-720 | 2.0 | 2.0 | 2.0 | 2.0 | 2.1 | 2.0 | 1.9 |
| Propylene Glycol USP | | 10.0 | | 7.0 | 7.0 | 7.0 | 7.0 |
| Milli-Q water | | | | 3.0 | 3.0 | 3.0 | 3.0 |
| DRAGOCO Green Tea Extra (powder) | | | | 5.0 | | | |
| DRAGOCO Grape Seed Extract | | | | | 1.0 | 5.0 | 10.0 |
| Glycerin | | | 5.0 | | | | |
| MP Diol Glycol | | | 10.0 | | | | |
| Abil WO 9 | | | 1.0 | | | | |
| DRAGOCO Green Tea Extract (liquid) | 30.0 | | | | | | |
| DRAGOCO Green Tea concentrate (powder) | | 5.0 | 5.0 | | | | |

In a second set of examples, botanical extract test compositions were prepared in water at 0.8 percent (w/v). Green tea extract and grape seed extract were purchased from Symrise, formerly DRAGOCO (Totowa, N.J.). In these studies, the EPIDERM cultures were removed from the incubator after 6 hours; a 100 microliter aliquot of the underlying medium was transferred to a 96 well plate and stored at −80° C. The cultures were placed back into the incubator and removed 18 hours later. After the 24 hour incubation, the underlying medium was removed and stored at −80° C. The irritation response of the EPIDERM skin culture to the botanical extract test compositions/control and either the fecal extract insult or fecal protease insult solution was determined by measuring the amount of IL-1α for both the 6 and 24 hours samples. Interleukin-1 alpha was quantified using an Interleukin-1 alpha Quantikine Kit available from R&D Systems of Minneapolis, Minn. Interleukin-1 alpha measurements were converted to $Log_{10}$ for each of the treatments and the averages for each treatment were calculated. To determine the ability of the extracted botanical test compositions to reduce skin irritation caused by either the fecal extract insult or fecal protease insult, the percent mean reduction of IL-1α was calculated as follows:

$$\% \text{ mean reduction of } IL-1\alpha = 100 \times \frac{((\text{Water} + \text{insult})\text{result} - (\text{test composition} + \text{insult})\text{result})}{((\text{Water} + \text{insult})\text{result} - (\text{Water} + \text{Water}/PBS)\text{result})}$$

(Test composition+insult)result=the measured amount of IL-1α from treatment with a botanical extract+ insult.

(Water+insult)result=the measured amount of IL-1α from a treatment with deionized water+insult.

(Water+Water/PBS)result=the measured amount of IL-1α from a treatment with deionized water+ deionized water or PBS.

The greater the percent mean reduction of IL-1α, the more effective the test composition was at reducing irritation caused by either the fecal protease insult or the fecal extract insult.

The effect of these test compositions at reducing skin irritation in the EPIDERM skin model induced by either the fecal protease insult or fecal extract insult is shown in Table 4.

TABLE 4

| Botanical Component of Aqueous Compositions | Mean Reduction of Interleukin-1 Alpha (percentage) (Fecal Protease Insult) | Mean Reduction of Interleukin-1 Alpha (percentage) (Fecal Extract Insult) |
|---|---|---|
| Green Tea- 6 hours | 89(3) | >100*(4) |
| Green Tea- 24 hours | 86*(5) | 73*(6) |
| Grape Seed- 6 hours | 92(3) | >100*(5) |
| Grape Seed- 24 hours | 94*(4) | 97*(6) |

*indicates the composition had a significant mean difference from the fecal protease insult or fecal extract insult, respectively, applying a Student's t-test with $p < 0.05$.

For each of the compositions in Table 4, mean reduction of the inflammatory marker (IL-1α) is shown. Replicates performed for each test composition are shown in parentheses. The percent mean IL-1α reduction results illustrate that green tea and grape seed botanical extracts (0.8%, w/v, in water) can both significantly reduce the irritation response caused by irritants from infant feces or a protease mixture (protease-like activities measured in feces). These data show that botanical extracts of the invention exhibit a skin protective effect as evidenced by a reduced irritation response caused by irritants in infant feces.

The reduction of IL-1α results in all examples were analyzed to statistically identify "outlier" results. The EPIDERM skin model is known to be variable with the variability attributed to differences in the culture, variation in the application of treatment and other uncontrollable factors. A statistical analysis technique was applied to identify when a result abnormally deviated from the rest of the data set. The irritation values were first converted to Log 10 in order to normalize the distribution (convert to a bell-shaped curve). After conversion, the values were analyzed for high or low value outliers; subsequently, the values were analyzed with a student's t-test to identify significant differences from the "control". The statistical analysis used to identify "outliers" is described on page 460 of the book, "Statistical Methods in Research and Production" edited by Owen L. Davies and Peter L. Goldsmith, published by Longman Group Limited, fourth revised edition published in 1984.

Compositions of the invention were also evaluated for their efficacy in a clinical study. The study was performed to measure the erythema response to application of an "insult" when the skin is treated with compositions of the invention. The petrolatum control and petrolatum test compositions used in this study are described in Table 5. Insult and saline only control sites were included with the four petrolatum composition sites. The study duration was twelve days, Monday through Saturday (no Sunday visit). Twenty healthy Caucasian participants were recruited who were between the ages of 18 and 60. Six test areas were marked on the upper backs of the study participants. This study involved a daily topical application of 10 microliters of petrolatum test composition to the skin followed by patching with 200 microliters of a protease/bile acid mixture ("insult") in a 2.5 cm diameter HILL TOP chamber fitted with a pad, representing a repeated biological insult. The protease/bile acid mixture was comprised of the following components in PBS: trypsin and chymotrypsin (available from Specialty Enzymes and Biochemicals Co. of Chino, Calif.) at a concentration of 1500 micrograms per milliliter, 6.5 milligrams per milliliter cholic acid sodium, 6.2 milligrams per milliliter deoxycholic acid sodium and 3.1 milligrams per milliliter chenodeoxycholic acid sodium (each acid is available from Sigma Chemical Company of St. Louis, Mo.). A control site to which only PBS was applied was also included in the study.

TABLE 5

| Component | A (Wt. %) | B (Wt. %) | C (Wt. %) | D (Wt. %) |
|---|---|---|---|---|
| Penreco Petrolatum USP | 100.0 | 80.0 | 80.0 | 80.0 |
| Gilugel EUG | | 3.0 | 3.0 | 3.0 |
| Cabot Cab-o-Sil MP-5 | | 2.0 | 2.0 | 2.0 |
| Propylene Glycol USP | | 10.0 | 10.0 | 10.0 |
| DRAGOCO Green Tea Extra (powder) | | 5.0 | | 2.5 |
| DRAGOCO Grape Seed Extract | | | 5.0 | 2.5 |

When the HILL TOP chambers containing the treated pads were placed on the designated, randomized test sites on the upper backs of the test participants, the chambers were covered with SCANPOR semi-occlusive tape. The chambers remained in place overnight. During each daily visit, the chambers were removed and the underlying skin was allowed to air dry for 15-20 minutes. After the drying period, each test and control site was visually assessed in a blinded manner by an expert grader. The expert graders made the visual assessments under consistent lighting and the graders used a scoring system of 0 (no erythema) to 3 (severe erythema with edema and vesicles). If a visual score of greater than or equal to 2 was observed for any test site, the site was no longer treated. Every day, test compositions were re-applied and the sites were repatched with new chambers containing 200 microliters of fresh solution. Since there was no Sunday visit, the chambers remained in place from Saturday to Monday.

The cumulative irritation scores are reported for each of the six sites in Table 6. The cumulative irritation scores are based on the highest erythema value obtained for a site; if a site reached a score of 2 or greater and was discontinued, the maximum score is carried forward through the end of the study. If a site reached a 2 and was discontinued, but had a score of 3 on the following day, the score of 3 was used for the cumulative calculation.

TABLE 6

| Composition | Test Site | Cumulative Irritation Score |
|---|---|---|
| | Saline site | 50.0 |
| | Insult site | 220.5 |
| A | Petrolatum site | 109.0 |
| B | Petrolatum + 5% green tea site | 72.0 |
| C | Petrolatum + 5% grape seed site | 85.0 |
| D | Petrolatum + 2.5% green tea and 2.5% grape seed site | 56.0 |

Mean score values reported in Table 7. below, were analyzed using ANOVA statistical analysis. The analyses showed that the petrolatum+5% green tea, petrolatum+5% grape seed, and the combination of petrolatum+2.5% green tea and 2.5% grape seed sites had significantly less erythema than the Insult and the Petrolatum sites. The petrolatum composition containing the combination of green tea and grape seed site performed better than either of the sites with the two botanicals alone and was not significantly different from the saline control site. The clinical study results support the efficacy of the compositions of the inventions for reducing the irritation response of the skin and for protecting the skin from irritants.

TABLE 7

| Composition | Test Site | Mean Irritation Score |
|---|---|---|
| | Saline site | 0.25 |
| | Insult site | 1.10 |
| A | Petrolatum site | 0.55 |
| B | Petrolatum + 5% green tea site | 0.36 |
| C | Petrolatum + 5% grape seed site | 0.43 |
| D | Petrolatum + 2.5% green tea and 2.5% grape seed site | 0.28 |

As evidenced by the experimental results and examples described herein, the compositions of the invention provide skin health benefits through enzyme inhibition and protective effects such that the irritation response of the skin is reduced. The benefits of the compositions of the invention are desirably achieved when the compositions are applied to the bodyside liner of an absorbent article. While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

We claim:

1. An absorbent article comprising:
    (a) an outer cover;
    (b) a liquid permeable bodyside liner that defines a bodyfacing surface and that is connected in superposed relation to the outer cover;
    (c) an absorbent body that is located between the bodyside liner and the outer cover; and
    (d) a composition on at least a portion of the bodyfacing surface of the bodyside liner that includes from about 50 to about 95 percent by weight of emollient, from about 1 to about 40 percent by weight of viscosity enhancer and from about 5 to about 30 percent by weight of extracted botanical active wherein the extracted botanical active is selected from grape seed, green tea, constituents of grape seed and green tea and mixtures of these actives.

2. The absorbent article of claim 1, wherein the emollient of the composition is selected from petrolatum, vegetable based oils, mineral oils, dimethicone, lanolin, glycerol esters, alkoxylated carboxylic acids, alkoxylated alcohols, fatty alcohols and mixtures thereof.

3. The absorbent article of claim 1, wherein the viscosity enhancer of the composition is selected from polyolefin resins, lipophilic/oil thickeners, ethylene/vinyl acetate copolymers, organically modified clays, polyethylene, silica, silica silylate, silica methyl silylate, colloidal silicone dioxide, alkyl hydroxy ethyl cellulose, microcrystalline wax, shellac wax, hexadecyl cosanyl hexacosanate, $C_{20}$-$C_{40}$ alkyl hydroxystearyl stearate, glycol montanate, ozokerite wax, polyperfluoromethylisopropylether montan wax and mixtures thereof.

4. The absorbent article of claim 1, wherein the composition further includes from about 5 to about 48 percent by weight of solidifying agent.

5. The absorbent article of claim 4 wherein the solidifying agent of the composition is selected from beeswax, behenyl behenate, behenyl benzoate, branched esters, candelilla wax, carnauba wax, synthetic carnauba wax, PEG-12 carnauba wax, cerasin, microcrystalline wax, hydrogenated microcrystalline wax, hexadecylcosanyl hexacosanate, polyperfluoromethylisopropylether montan wax, alkylmethylsiloxanes, glycol montanate, jojoba wax, lanolin wax, ozokerite, paraffin, synthetic paraffin, polyethylene, $C_{20}$-$C_{40}$ alkyl hydroxystearyl stearate, $C_{30}$ alkyl dimethicone, cetyl esters, zinc stearate, shellac wax, hydrogenated cottonseed oil, hydrogenated squalene, hydrogenated jojoba oil and mixtures thereof.

6. The absorbent article of claim 1 wherein the composition further includes from about 0.1 to about 48 percent by weight of natural fats or oils.

7. The absorbent article of claim 6, wherein the natural fat or oil is selected from Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

8. The absorbent article of claim 1 wherein the composition further includes from about 0.1 to about 10 percent by weight of sterols or sterol derivatives.

9. The absorbent article of claim 8, wherein the sterol or sterol derivative is selected from cholesterol, sitosterol, stigmasterol, and ergosterol, as well as $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanosterol, soy sterol, avocado sterols, sterol esters and mixtures thereof.

10. The absorbent article of claim 1, wherein the composition further includes from about 0.5 to about 20 percent by weight of a rheology modifier.

11. The absorbent article of claim 10, wherein the rheology modifier is selected from silica, silica silylate, silica methyl silylate, quaternary starch compounds, quaternary modified clays, organically modified clays and mixtures thereof.

12. An absorbent article comprising:
 (a) an outer cover;
 (b) a liquid permeable bodyside liner that defines a bodyfacing surface and that is connected in superposed relation to the outer cover;
 (c) an absorbent body that is located between the bodyside liner and the outer cover; and
 (d) a composition on at least a portion of the bodyfacing surface of the bodyside liner that includes from about 50 to about 95 percent by weight of emollient, from about 1 to about 40 percent by weight of viscosity enhancer and from about 2.5 to about 5 percent by weight of extracted botanical active wherein the extracted botanical active is selected from grape seed, constituents of grape seed, and mixtures of these actives.

13. The absorbent article of claim 12 wherein the composition includes at least 2.5% by weight grape seed extract and the composition further includes at least 2.5% by weight green tea extract.

14. The absorbent article of claim 1 wherein the composition includes at least 2.5% by weight grape seed extract and at least 2.5% by weight green tea extract.

* * * * *